US008815808B2

(12) United States Patent
Nykjaer et al.

(10) Patent No.: US 8,815,808 B2
(45) Date of Patent: *Aug. 26, 2014

(54) MODULATION OF ACTIVITY OF NEUROTROPHINS

(75) Inventors: Anders Nykjaer, Risskov (DK); Claus Munck Petersen, Aarhus C (DK)

(73) Assignee: H. Lundbeck A/S, Valby (DK)

( * ) Notice: Subject to any disclaimer, the term of this patent is extended or adjusted under 35 U.S.C. 154(b) by 154 days.

This patent is subject to a terminal disclaimer.

(21) Appl. No.: 13/253,238

(22) Filed: Oct. 5, 2011

(65) Prior Publication Data

US 2012/0082671 A1   Apr. 5, 2012

Related U.S. Application Data

(62) Division of application No. 10/539,443, filed as application No. PCT/DK03/00919 on Dec. 19, 2003, now Pat. No. 8,066,997.

(30) Foreign Application Priority Data

Dec. 20, 2002   (DK) .................................. 200201977

(51) Int. Cl.
| | | |
|---|---|---|
| A61K 39/395 | (2006.01) | |
| A61K 49/16 | (2006.01) | |
| A61K 38/17 | (2006.01) | |
| A61K 38/08 | (2006.01) | |
| C07K 14/48 | (2006.01) | |
| C07K 14/475 | (2006.01) | |
| C07K 16/18 | (2006.01) | |
| C07K 16/28 | (2006.01) | |
| A61K 38/00 | (2006.01) | |

(52) U.S. Cl.
CPC ........... *A61K 38/179* (2013.01); *A61K 39/3955* (2013.01); *A61K 38/08* (2013.01); *C07K 14/48* (2013.01); *A61K 38/00* (2013.01); *A61K 38/177* (2013.01); *C07K 14/475* (2013.01)
USPC ..................... 514/17.7; 424/139.1; 530/387.1

(58) Field of Classification Search
None
See application file for complete search history.

(56) References Cited

U.S. PATENT DOCUMENTS

| | | | |
|---|---|---|---|
| 5,516,772 A | 5/1996 | Glicksman et al. | |
| 6,011,004 A | 1/2000 | Kessler et al. | |
| 6,291,247 B1 | 9/2001 | Riopelle et al. | |
| 6,300,327 B1 | 10/2001 | Knusel et al. | |
| 6,333,310 B1 | 12/2001 | Presta et al. | |
| 6,417,159 B1 | 7/2002 | Riopelle et al. | |
| 2001/0046956 A1 | 11/2001 | Hadcock | |

FOREIGN PATENT DOCUMENTS

| | | |
|---|---|---|
| EP | 0994188 A1 | 4/2000 |
| EP | 1891966 A1 | 2/2008 |
| WO | 98/46254 A1 | 10/1998 |
| WO | 00/44396 A1 | 8/2000 |
| WO | 01/49313 A1 | 7/2001 |
| WO | 02/096356 A2 | 12/2002 |

OTHER PUBLICATIONS

Triguero, et al.; "Blood-brain barrier transport of cationized immunoglobulin G: enhanced delivery compared to native protein"; Proc. Natl. Acad. Sci. USA 86:4761-4765 (1989).
Vincent, J.-P., et al. "Neurotensin and neurotensin receptors"; TiPS. 20 (7):302-309 (1999).
Volosin, et al. "Interaction of survival and death signaling in basal forebrain neurons: roles of neurotrophin and proneurotrophins." The Journal of Neuroscience 26(29): 7756—(2006).
Wiesmann , C. and A.M. de Vos; "Nerve growth factor: structure and function"; Cell. Mol. Life Sci. 58, 758-759 (2001).
Wilcox, et al.; Intracranially administered anti-Aβ antibodies reduce β-amyloid deposition by . . . , The Journal of Neuroscience 23(9):3745-3751 (2003).
Yano, et al.; "Neurotrophin receptor structure and interactions"; Pharmaceutica Acta Helvetiae 74:253-260. (2000).
Airaksinen and Saarma; "The GDNF family: Signaling. Biological functions and therapeutic value"; Nature Reviews—Neuroscience; 3:383-394 (2002).
Antonelli et al.; "Neurotensin Enhances Glutamate Excitotixicity in Mesencephalic Neurons in Primary Culture"; Journal of Neuroscience Research 70: 766-773 (2002).
Appel, S.H.; "A unifying hypothesis for the cause of amytrophic lateral sclerosis, parkinsonism, and Alzheimer's disease"; Ann. Neurol. 10, 499-505 (1981).
Arshaysky, Y.I.; "Alzheimer's disease, brain immune privilege and memory: a hypothesis"; J. Neural Transm.; 113:1697-1707 (2006).
Ballabh, et al.; "The blood-brain barrier: an overview structure, regulation and clinical implications"; Neurobiology of Disease; 16:1-13 (2004).

(Continued)

*Primary Examiner* — Daniel E Kolker
*Assistant Examiner* — Stacey N MacFarlane
(74) *Attorney, Agent, or Firm* — Mary Catherine Di Nunzio

(57) ABSTRACT

The present invention relates to methods for modulating the activity of one or more neurotrophins, such as neural growth factor (NGF), brain derived neurotrophic factor (BDNF), neurotrophin-3 (NT-3), and neurotrophin-4 (NT-4), in an animal and methods for treatment of a disease or disorder in an individual by modulation of neurotrophin activity. The modulation is carried out by interfering with binding between a neurotrophin and a receptor of the Vps10p-domain receptor family or modulating the expression of a receptor of the Vps10p-domain receptor family.
Methods for screening for agents capable of modulating neurotrophin activity and agents selected using these screening methods are also disclosed, as are methods for determining the effect of an agent on one or more neurotrophins in cells. The present invention also pertains to methods for modulating the transport of one or more neurotrophins.

8 Claims, 7 Drawing Sheets

(56) References Cited

OTHER PUBLICATIONS

Beattie et al., ProNGF Induces p-75-Mediated Death of Oligodendrocytes following Spinal Cord Injury, Neuron; 36(3): 375-86 (Oct. 24, 2002).
Bibel, et al.; "Biochemical and functional interactions between the neurotrophin receptors trk and p75NTR"; EMBO Journal 18(3):616-622 (1999).
Bickel, Ulrich; "Antibody delivery through the blood-brain barrier"; Advanced Drug Delivery Reviews; 15:53-72 (1995).
Bigner, et al.; "Phase I studies of treatment of malignant gliomas and neoplastic meningitis with 131I-radiolabeled monoclonal antibodies anti-tenascin 81C6 and anti-chondroitin proteoglycan sulfate Mel-14 F(ab')2—a preliminary report."; Journal of Neuro-Oncology 24:109-122 (1995).
Boules et al., "Antiparkinson-like effects of a novel neurontensin analog in unilaterally 6-hydroxydopamine lesioned rats", European Journal of Pharmacology 428; 227-233 (2001).
Chao, Moses V.; "Neurotrophin Receptors: A Window into Neuronal Differentiation"; Neuron, 9: 583-593 (1992).
Chao, Moses and Mark Bothwell "Neurotrophins: to cleave or not the cleave"; Neuron 33, 9-12 (Jan. 3, 2002).
Chao, Moses V.; "Neurotrophins and their receptors: a convergence point for many signaling pathways"; Nature Reviews—Neuroscience; 4:299-309 (2003).
Chen, et al. "The proNGF-p75 NTR—sortilin signaling complex as new target for the thera peutic treatment of Parkinson's Disease"; CNS Neurol Disord Drug Targets; 7:512-523 (2008).
DeBoer, et al.; Blood-brain barrier dysfunction and recovery.; Journal of Neural Transmission; 113:455-462 (2006).
Dechant, George; "Molecular interactions between neurotrophin receptors"; Cell Tissue Res 305:229-238; (2001).
Duman et al.; "A Molecular and Cellular Theory of Depression"; Arch. Gen. Psychiatry 54, 597-606 (1997).
Fahnestock, Margaret et al.; "The Precursor Pro-Nerve Growth Factor is the Predominant Form of Nerve Growth Factor in Brain and is increased in Alzheimer's Disease"; Mol. Cell. Neurosci., San Diego, US, 18, 210-220, XP002294169, ISSN: 1044-7431 (Aug. 1, 2001).
Fan, et al.; "Differential effects of pro-BDNF on sensory neurons after sciatic nerve transection in neonatal rats"; European Journal of Neuroscience 27:2380-2390 (2008).
French and Tschopp; "Protein-based therapeutic approaches targeting death receptors"; Cell Death and Differentiation; 10:117-123 (2003).
Friden, et al.; "Anti-transferring receptor antibody-drug conjugates cross the blood-brain barrier"; Proc. Natl. Acad. Sci. USA 88:4771-4775 (1991).
Hampe, Wolfgang et al.; "The genes for the human VPS10 domain-containing receptors are large and contain many small exons"; Human Genetics, Berlin, DE, vol. 108, No. 6 108,529-536, XP002294173, ISSN:034-6717 (Jun. 1, 2001).
Harrington et al., PNAS; 101(16): 6226-30 (Apr. 20, 2004).
Hempstead, Barbara L.; "The many faces of p75NTR"; Curr Opin. Neurobiol, 12(3):260-7 (Jun. 2002).
Jacobsen et al.; "Molecular characterization of a novel human hybrid-type receptor that binds the α2-macroglobulin receptor-associated protein" J. Biol. Chem. 271, 31379-31383 (Dec. 6, 1996).
Jacobsen et al.; "Activation and Functional Characterization of the Mosaic Receptor SorLA/LR11", J. Biol. Chem. 271 (25) 22788-22796 (Jun. 22, 2001).
Kitabgi, P. "Target neurotensin receptors with agonists and antagonists for therapeutic purposes", Curr. Opin. in Drug Discovery & Development, 5(5):764-776 (2002).
Lashford, et al.; "A pilot study of 131I monoclonal antibodies in the therapy of leptomeningeal tumors"; Cancer 61-857-868 (1988).
Lee, et al. "Regulation of cell survival by secreted proneurotrophins". Science 294, 1945-1948 (Nov. 3, 2001).
Lee, et al.; "The uniqueness of being a neurotrophin receptor"; Curr. Opin. Neurobiol. 11, 281-286 (2001).
Lin et al.; "Sortilin is a major protein component of Glut4-containing vesicles"; Journal of Biological Chemistry, 272 (39); 24145-47 (1997).
Mazella et al.; "The 100-kDa neurotensin receptor is gp95/sortilin, a non-G-Protein-coupled receptor";.J.Biol. Chem. 273, 26273-26276 (Oct. 9, 1998).
Mazella J. "Sortilin/neurotensin receptor-3: a new tool to investigate neurotensin signaling and cellular trafficking?" Cellular Signaling, 13:1-6, (Jan. 2001).
Munck Petersen, et al. "Propeptide cleavage conditions sortitlin/neurotensin receptor-3 for ligand binding"; The EMBO Journal 18, 595-604 (1999).
Miller, F.D. and D.R. Kaplan; "Neurotrophin signaling pathways regulating neuronal apoptosis"; Cell. Mol. Life Sci. 58, 1045-1053 (2001).
Neet, K.E. and R.B. Campenot; "Receptor binding Internalization, and retrograde transport of neurotrophic factors"; Cell. Mol. Live Sci. 58, 1021-1035 (2001).
Neuwelt, Edward A.; "Mechanism of disease: the blood-brain barrier"; Neurosurgery 54:131-142 (2004).
Nielsen et al.; "The sortilin cytoplasmic tail conveys Golgi-endosome transport and binds the VHS domain of the GGA2 sorting protein"; The EMBO Journal 20(9): 2180-2190 (2001).
Nielsen et al.; "Sortillin/Neurotensin Receptor-3 Binds and Mediates Degradation of Lipoprotein Lipase", The Journal of Biological Chemistry, 274 (13):8832-8836 (Mar. 26, 1999).
Nykjaer et al.; "p75NTR—live or let die"; Current Opinion in Neurobiology, vol. 15, pp. 49-57 (2005).
Nykjaer, et al.; "Sortilin is essential for proNGF-induced neuronal cell death"; Nature, Nature Publishing Group, London UK, vol. 427, 427:843-848 XP002286438, ISSN: 0028-0836 (Feb. 26, 2004).
Pardridge, William M.; "Drug targeting to the brain"; Pharmaceutical Research 24(9):1733-1744 (Sep. 2007).
Petersen et al.; "Molecular identification of a novel candidate sorting receptor purified from human brain by receptor—associated protein"; J. Biol. Chem. 272, 3599-3605 (Feb. 7, 1997).
Raffioni et al.; "The Receptors for Nerve Growth Factor and other Neurotrophins"; Ann. Rev. Biochem. 62, 823-850 (1991).
Rattenholl et al.; "The pro-sequence facilitates folding of human nerve growth factor from *Escherichia coli* inclusion bodies"; Eur. J. Biochem. 268, 3296-3303 (2001).
Rubenstein, et al.; "Rituximab therapy for CNS lymphomas: targeting the leptomeningeal compartment"; Blood 101 (2):466-468 (2003).
Rubin and Staddon; "The cell biology of the blood-brain barrier"; Annu.Rev Neurosci. 22:11-28 (1999).
Shapiro et al., "I-chTNT-1/B mAb" tumour necrosis therapy for malignant astrocytic glioma Expert Opinion in Biological Therapy, 6(5); 541,545, (2006).
Shirayama et al.; "Brain-derived neurotrophic factor produces antidepressent effects in behavioral models of depression"; J. Neurosci. 22, 3251-3261 (Apr. 15, 2002).
Thoenen; "The changing scene of neurotrophic factors"; Trends Neurosci. 14, 165-170 (1991).
Lee, et al.; 2001, "The uniqueness of being a neurotrophin receptor"; Curr. Opin. Neurobiol. 11, pp. 281-286.
Massa, S.M. et al., 2003, "Alzheimer's Therapeutics," J. Molec. Neurosci 20, pp. 323-326.
Miller, F.D. et al., 2001 "Neurothrophin signaling pathways regulating neuronal apoptosis" Cell. Mol. Life Sci. 58, 1045-1053.

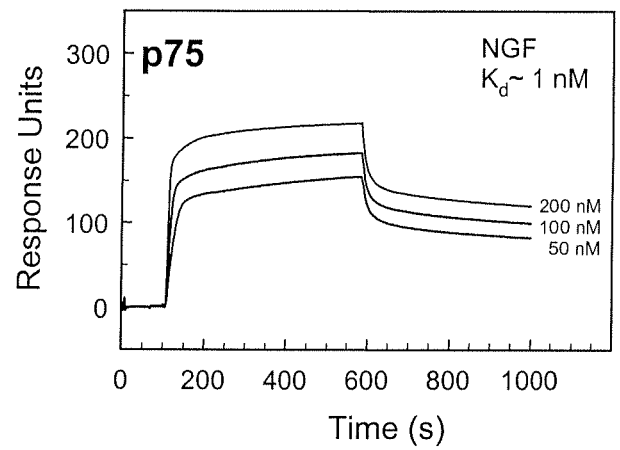
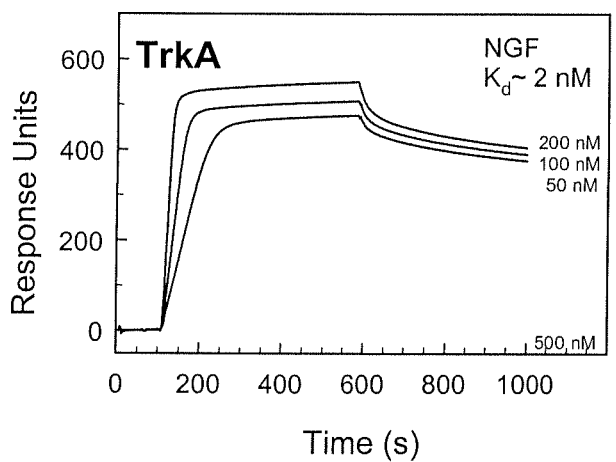
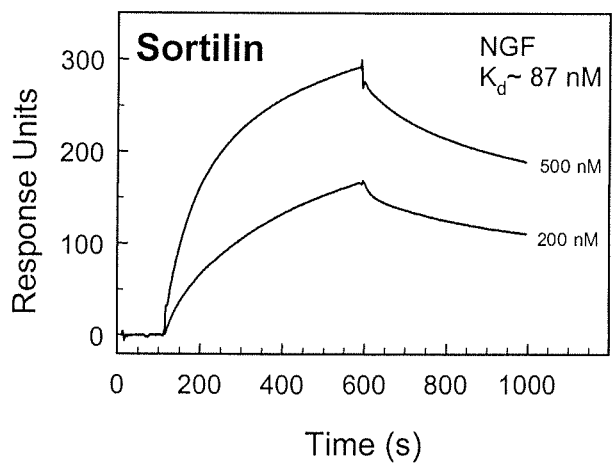
Fig. 2

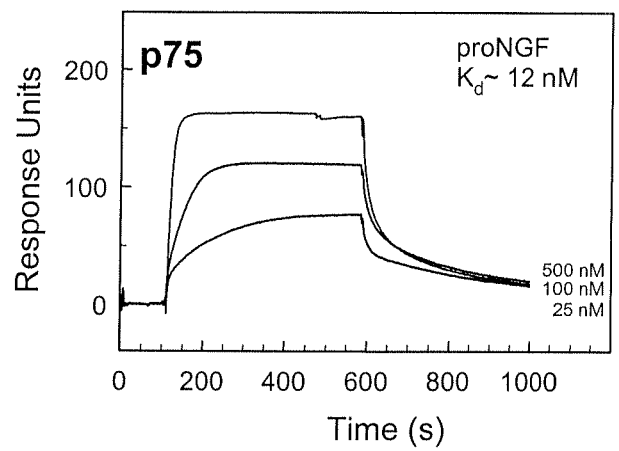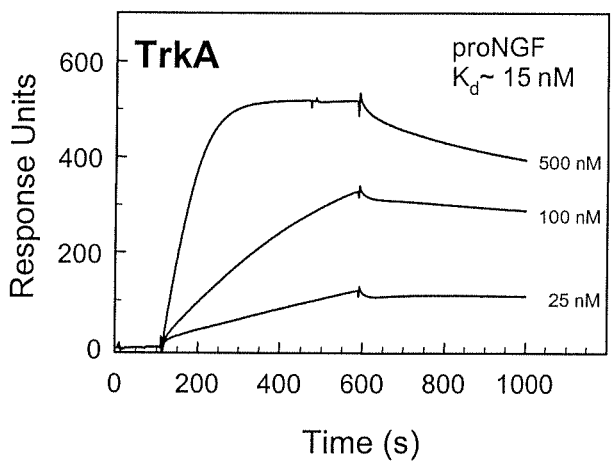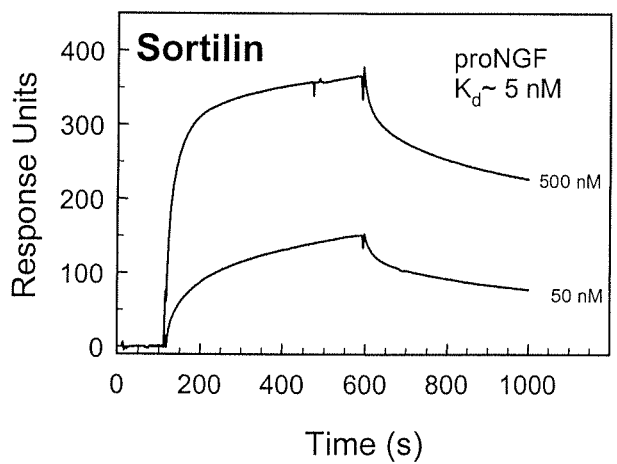
Fig. 3

Fig. 6
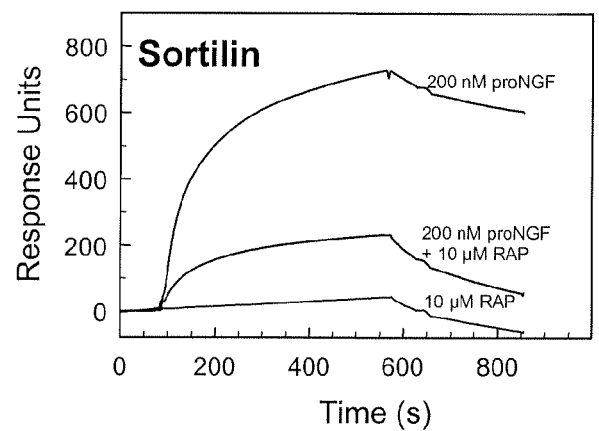
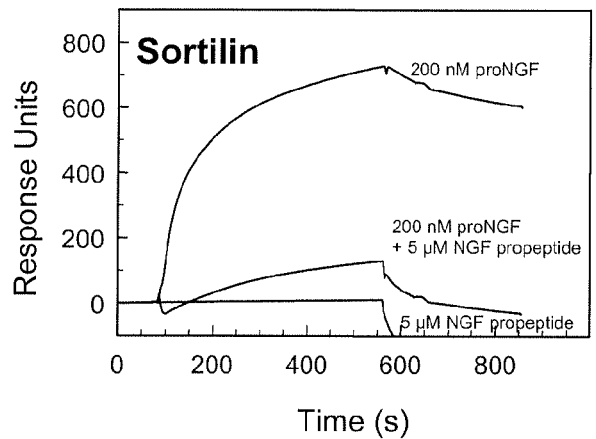
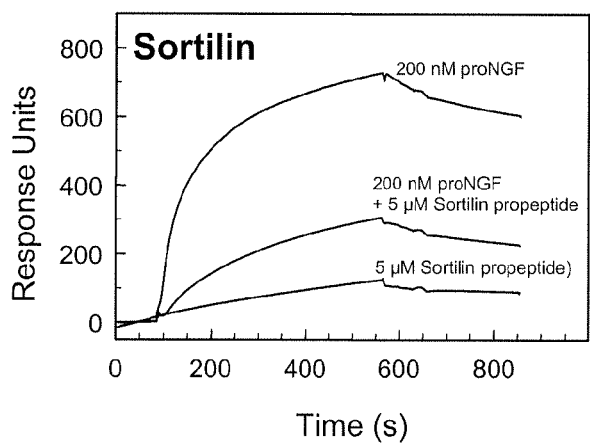

MODULATION OF ACTIVITY OF NEUROTROPHINS

This application is a divisional of U.S. application Ser. No. 10/539,443 filed Jun. 20, 2005, which is a 371 National Phase of PCT/DK03/000919, filed Dec. 19, 2003, which claims foreign priority under 35 U.S.C. §119(a)-(d) of Danish Patent Application No. PA200201977, filed Dec. 20, 2002. The entirety of each of the aforementioned applications is hereby incorporated by reference.

All patent and non-patent references cited in the application, or in the present application, are also hereby incorporated by reference in their entirety.

FIELD OF INVENTION

The present invention relates to compositions which are useful in modulating neurotrophin activity, as well as methods for the preparation and use thereof. Methods are also provided for screening for agents for use in said compositions.

BACKGROUND OF INVENTION

The Neurotrophin Family

Neurotrophins are dimeric peptide hormones. The first member of the neurotrophin family to be discovered was nerve growth factor (NGF), which plays an important role in processes such as the development of sensory and sympathetic neurons of the peripheral nervous system (Levi-Montalcini, R. and Angeleeti, P. U:, Physiol. Rev. 48, 534-569 (1968)). The next member of the neurotrophin family to be isolated was brain-derived neurotrophic factor (BDNF), also referred to as neurotrophin-2 (NT-2), the sequence of which was published by Leibrock, J. et al. in 1989 (Nature 341, 149-152). In 1990 several groups identified a neurotrophic factor originally called neuronal factor (NF), now referred to as neurotrophin-3 (NT-3) (Ernfors et al., Proc. Natl: Acad. Sci. USA 87, 5454-5458 (1990); Hohn et al., Nature 344, 339; Maisonpierre et al., Science 247, 1446; Rosenthal et al., Neuron 4, 767; Jones and Reichardt, Proc. Natl. Acad. Sci. USA 87, 8060-8064; Kaisho et al., FEBS Lett. 266, 187). Neurotrophins-4 and -5 were then added to the family (Neuron 6, 845-858 (1991); Berkmeier, L. R. et al., Neuron 7, 857-866 (1991); Ip et al., Proc. Natl. Acad. Sci. USA 89, 3060-3064 (1992)).

Receptors for the Neurotrophin Family

In a similar way to other polypeptide growth factors, neurotrophins affect their target cells through interactions with cell surface receptors. According to current knowledge, neurotrophins bind to two discrete receptor types which can be distinguished pharmacologically: the Trk and $p75^{NTR}$ neurotrophin receptors. $p75^{NTR}$ is a member of the Fas/tumour necrosis factor (TNF) receptor family, and can interact with all the mammalian members of the neurotrophin family with equal affinities (Rodriguez-Tebar et al. 1990, Neuron 4:487-492; Barker and Murphy, 1992, Mol. Cell. Biochem. 100:1-15). Cells expressing TrkA, a tyrosine kinase receptor originally identified as a human oncogene (Mltin-Zanca et al, Nature 319:743-748) bind solely to NGF and exhibit significantly slower dissociation kinetics (Jing et al. 1992, Neurol. 9:1067-1079; Loeb and Greene, 1993, Neuroscience 13:2919-2929). BDNF binds the TrkB receptor only, but NT-3 can bind all three Trk (A, B and C) receptors, with a preference for TrkC. NT-4/5 can bind both TrkA and TrkB (Ip et al. PNAS 89:3060-3064; Klein et al. Neuron 9:947-956). NT-7 does not interact with TrkB or TrkC but can however induce tyrosine phosphorylation of TrkA, indicating a similar receptor specificity as NGF (Nilsson et al., FEBS Lett (1998) March 13; 424 (3):285-90). Recombinant purified NT-6 also has a spectrum of actions similar to NGF but with a lower potency (Gotz et al., Nature (1994) November 17; 372 (6503):266-9).

The Neurotrophin Family: Precursor Proteins

The biology of the neurotrophin family is complex: the neurotrophins are synthesised intracellularly as 30-35 kDa precursor proteins, containing a signal peptide and glycosylation sites. During processing precursor proteins are also cleaved at a di-basic cleavage site by the calcium-dependent serine protease furin and other members of the prohormone convertase family, within the Golgi apparatus. The N-terminal part of this cleavage is the mature neurotrophin of 118-120 amino acids and a biologically active 12-14 kDa C-terminal product (Seidah et al, Biochem. J. (1996) 314:951-960).

Clinically Relevant Roles of the Neurotrophin Family

Neurotrophins are of clinical interest as they play an important role in neuronal cell survival and differentiation (Thoenen 1991, Trends Neurosci. 14: 165-170; Raffioni et al. 1991, Ann. Rev. Biochem. 62:823-850; Chao, 1992, Neuron 9:583-593; Barbacid 1993, Oncogene 8:2033-2042). Trk receptors transmit signals promoting neuronal survival, whereas $p75^{NTR}$ can induce neuronal apoptosis as well as neuronal survival depending on any co-expression of TrkA (Miller et al., Cell. Mol. Life Sci. 58:1045-1053 (2001)). Certainly, it has been demonstrated that activation of TrkA receptors can negate the proapoptotic effect of $p75^{NTR}$ (Yoon et al., J. Neurosci. (1998) 18:3273-3281).

It is probable that the propeptides of neurotrophins play important biological roles: at least one neurotrophin precursor protein (proNGF) and its proteolytically processed and mature counterpart (NGF) product differentially activate pro- and anti-apoptotic cellular responses through preferential activation of $p75^{NTR}$ and TrK receptors, respectively—proNGF having enhanced affinity for $p75^{NTR}$ receptors and a reduced affinity for Trk receptors relative to the mature forms of NGF. Indeed, it has been demonstrated that pro-NGF induces $p75^{NTR}$-dependent apoptosis in cultured neurons with minimal activation of TrkA-mediated differentiation or survival (Lee et al., Science (2001), 294:1945-1948).

Furthermore, neurotrophins are of clinical interest as it is known that both up-regulation of neurotrophins and increased $p75^{NTR}$ expression occur under pathological and inflammatory conditions, especially after nerve injury and damage to the vascular system. Indeed, Soilu-Hanninen et al. have demonstrated that the pro-apoptotic functions of $p75^{NTR}$ are directly implicated in injury-induced apoptosis (Soilu-Hanninen et al., J. Neurosci. 19:4824-4838 (1999)). Recently, it was also demonstrated that proNGF induces p75 mediated death of oligodendrocytes following spinal cord injury (Beatty et al., Neuron (2002), vol. 36, pp. 375-386).

It has been hypothesized that the lack of neurotrophic factors is responsible for the degeneration of selective neuronal populations as it occurs in Parkinson's disease, Alzheimer's disease and amyotrophic lateral sclerosis, and that application of corresponding neurotrophic factor might prevent neuronal degeneration [Appel, S. H., "A unifying hypothesis for the cause of amyotrophic lateral sclerosis, parkinsonism, and Alzheimer's disease," Ann. Neurol. 10:499-505 (1981)]. In particular, as NGF is a trophic factor for the population of basal forebrain cholinergic neurons which degenerates in Alzheimer's disease, it has been speculated that NGF may be useful in the treatment of this disease.

Another reason for interest in targeting neurotrophin pathways for therapy is that studies have provided supporting evidence for the involvement of neurotrophins in depression and antidepressant action (Duman et al. Arch Gen Psychiatry (1997) 54:597-606); for instance infusion of BDNF into the hippocampus has produced an antidepressant effect in two behavioural models of depression (Shirayama et al. (2002), J Neurosci 22 (8): 3251-3261).

The Vps10p-Domain Receptor Family

Sortilin (or NTR-3 or GP95) is a type I membrane receptor expressed in a number of tissues, including the brain, spinal cord, testis and skeletal muscle (Petersen et al., J. Biol. Chem., 272:3599-3605 (1997); Herman-Borgmeyer et al., Mol. Brain Res., 65:216-219 (1999)). Sortilin belongs to a family of receptors comprising Sortilin, SorLA (Jacobsen et al., J. Biol. Chem., 271:31379-31383 (1996)), SorCS1, SorCS2 and SorCS3. All the receptors in this family share the structural feature of an approximately 600-amino acid N-terminal domain with a strong resemblance to each of the two domains which constitute the luminal portion of the yeast sorting receptor Vps10p (Marcusson, E. G., et al., Cell, 77:579-586 (1994)). The Vps10p-domain comprises a C-terminal segment containing 10 conserved cysteines and an N-terminal propeptide of 40-80 amino acids.

In Sortilin, the propeptide exhibits high affinity binding to the fully processed receptor. Prevention of propeptide cleavage essentially inhibits ligand binding to Sortilin, indicating that the propeptide sterically hinders ligands from gaining access to their binding sites on the receptor (Petersen et al., EMBO J., 18:595-604, 1999).

Some progress has been made as to an understanding of the role of this family: there is evidence suggesting that Sortilin at least contains YXXφ and dileucine motifs, conforming to potent signals for Golgi-endosome sorting (Nielsen et al., EMBO 20 (9):2180-2190). It is probable that the other members of the family may also fulfil a similar "sorting" function, not least because they all exhibit homology to Vsp10p, the sorting receptor for carboxypeptidase Y (CPY) in yeast. Only a small proportion of Sortilin receptors are present on the cell surface (Mazella et al. J. Biol. Chem. (1998) 273, 26273-26276; Morris et al. J. Biol. Chem. (1998) 273:3582-3587), although expression on the surface membrane can be upregulated by stimuli including insulin in 3T3-L1 adipocytes (Morris et al. J. Biol. Chem. (1998) 273:3582-3587) and neurotensin in embryonic neurons (Chabry et al., J. Biol. Chem. (1993), 286:17138-17144).

Modulating Neurotrophin Activity: the Current State of the Art

Certainly, current understanding of the biological roles of neurotrophins makes the neurotrophin family an attractive target for therapeutic intervention, and some methods for modulation of neurotrophin activity are known:
1) U.S. Pat. No. 6,417,159 discloses a method for enhancing the effect of a neurotrophin with analogues of p75NTR367-379.
2) U.S. Pat. No. 6,300,327 describes compositions and methods for potentiation of neurotrophin activity.
3) U.S. Pat. No. 6,291,247 discloses methods of screening for factors that disrupt neurotrophin conformation and reduce neurotrophin biological activity.
4) U.S. Pat. No. 5,516,772 describes K-252 derivatives which enhance neurotrophin-induced activity.

SUMMARY OF INVENTION

The present invention relates to methods for modulating the activity of one or more neurotrophins in an animal and methods for treatment of a disease or disorder in an individual by modulation of neurotrophin activity. Accordingly, in one aspect the present invention relates to a method for modulating the activity of at least one neurotrophin and/or a proneurotrophin in an animal comprising administering to said animal a sufficient amount of an agent capable of
  (i) binding to a receptor of the Vps10p-domain receptor family and/or
  (ii) interfering with binding between a receptor of the Vps10p-domain receptor family and a neurotrophin and/or proneurotrophin and/or
  (iii) modulating the expression of a receptor of the Vps10p-domain receptor family Methods for screening for agents capable of modulating neurotrophin activity and agents selected using these screening methods are also disclosed, as are methods for determining the effect of an agent on one or more neurotrophins in cells. The present invention also pertains to methods for modulating the transport of one or more neurotrophins.

DESCRIPTION OF DRAWINGS

FIG. 2: Characterization of NGF binding to p75, TrkA, and Sortilin as measured by surface plasmon resonance analysis (BIAcore). Binding of 50-500 nM NGF was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively—were recorded and the Kd values for NGF binding were calculated to ~1 nM for p75, ~2 nM for TrkA, and ~87 nM for Sortilin.

Mature murine NGF was from Austral Biologicals (San Ramon, Calif.), recombinant human p75 neurotrophin receptor/Fc and human TrkA/Fc chimeras were from R&D systems (Oxon, UK). Human Sortilin was produced in stably transfected CHO-cells and purified as described elsewhere (Munck Petersen et al, EMBO J. (1999) 18:595-604).

FIG. 3: Characterization of proNGF binding to p75, TrkA, and Sortilin as measured by surface plasmon resonance analysis (BIAcore). Binding of 25-500 nM proNGF was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively—were recorded and the Kd values for proNGF binding were calculated to ~12 nM for p75, ~15 nM for TrkA, and ~5 nM for Sortilin.

Human recombinant proNGF was produced and purified in E. coli as described (Rattenholl et al, Eur. J. Biochem. (2001) 268:3296-3303). All other reagents were as described in the legend to FIG. 2.

Figure 4:
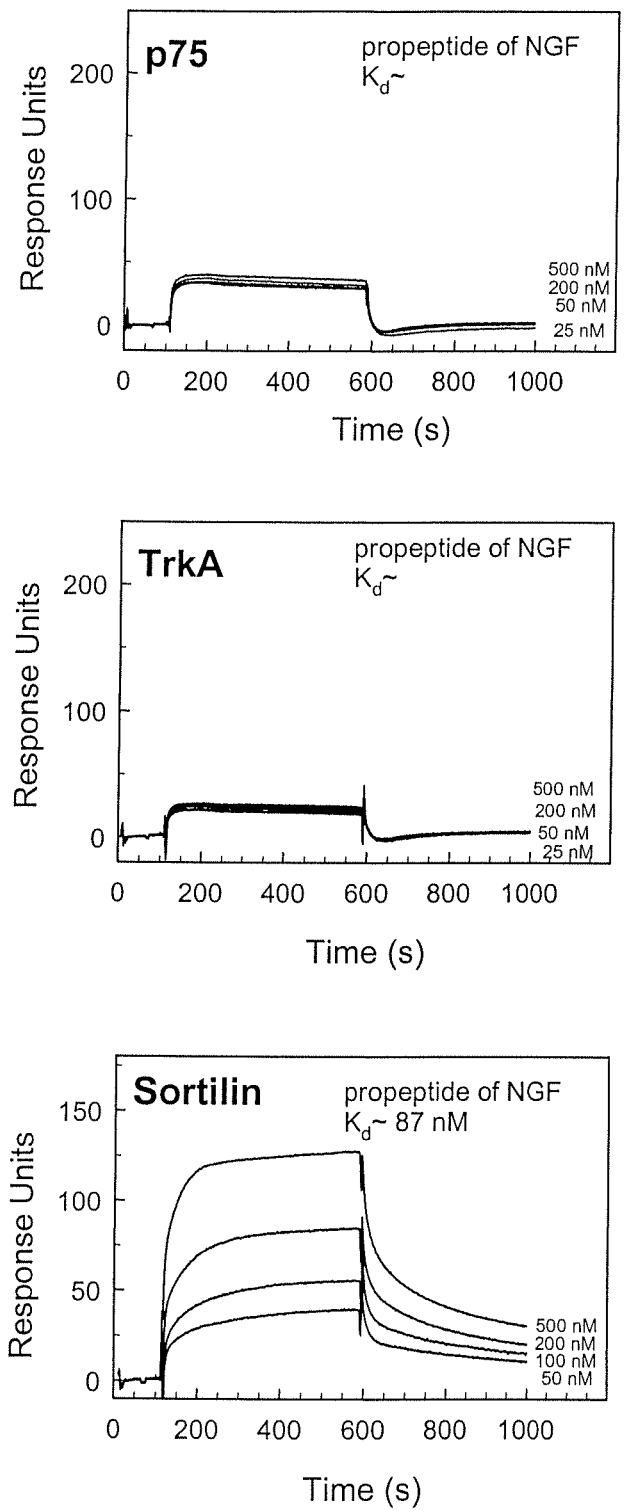

FIG. 4: Characterization of binding of the proNGF propeptide to p75, TrkA, and Sortilin as measured by surface plasmon resonance analysis (BIAcore). Binding of 25-500 nM propeptide was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively—were recorded and the Kd values for proNGF propeptide binding were calculated to ~87 nM for Sortilin. There was no detectable binding to p75 and TrkA.

The human NGF-propeptide expressed in E. Coli was provided by Elisabeth Schwarz, Martin-Luther-Universität Halle-Wittenberg, Halle/Saale, Germany. All other reagents were as described in the legends to FIGS. 2 and 3.

Figure 5:
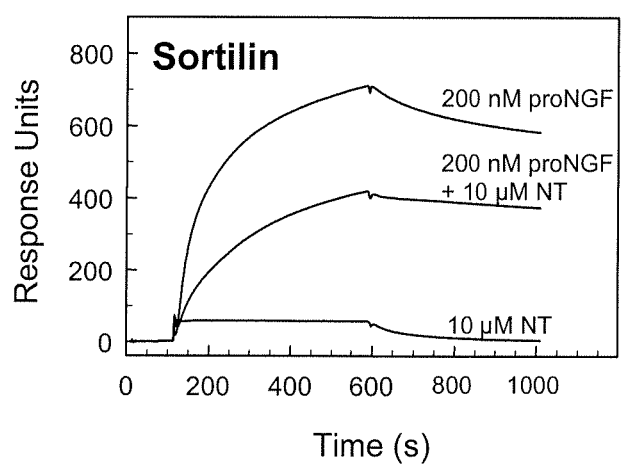

FIG. 5: Inhibition of proNGF binding to immobilized Sortilin by neurotensin as measured by BIAcore analysis. Binding of 200 nM proNGF to 51 fmol/mm$^2$ immobilized Sortilin is inhibited by ~45% following coinjection with 10 µM neurotensin. Binding of neurotensin alone is shown for comparison.

Neurotensin was obtained from Sigma-Aldrich (St. Louis, Mo.). All other products were as indicated above.

FIG. 6: Inhibition of proNGF binding to immobilized Sortilin by RAP (receptor-associated protein), the propeptide of proNGF, and the Sortilin propeptide. The inhibitors were prebound to Sortilin followed by coinjection with 200 nM proNGF. The baselines have been corrected for the signals obtained in the presence of each of the inhibitors. Maximal proNGF binding is measured without preincubation with the respective inhibitors. Binding of 200 nM proNGF to 51 fmol/mm$^2$ immobilized Sortilin is inhibited ~65% by 10 µM RAP, ~85% by 5 µM og the proNGF propeptide and ~65% by 5 µM the Sortilin propeptide.

Figure 7:
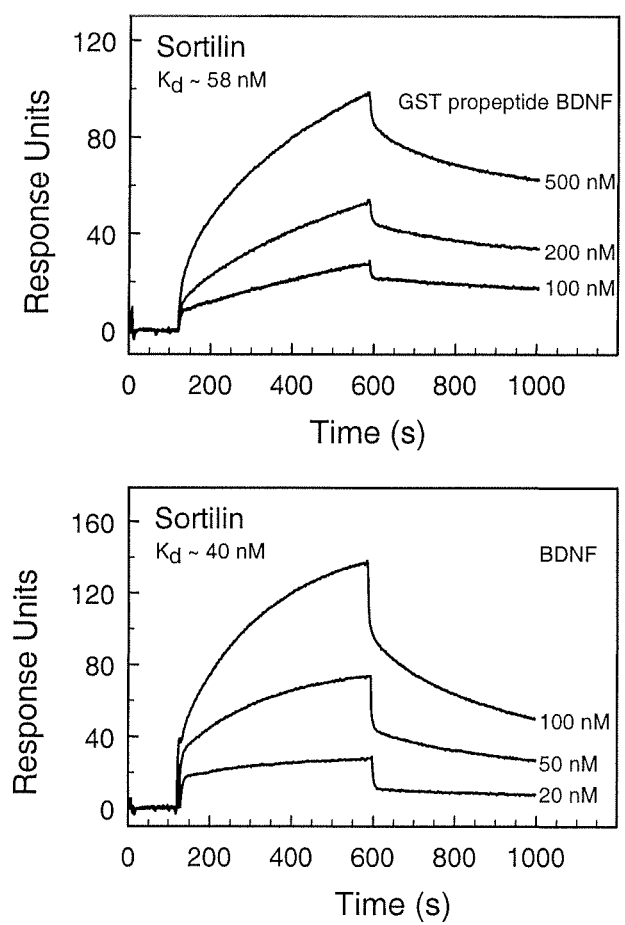

FIG. 7: Characterization of binding of BDNF and the prodomain of proBDNF to purified Sortilin as measured by surface plasmon resonance (BIAcore). Mature recombinant human BDNF was from Promega (#G1491) and the prodomain of human BDNF fused to GST (glutathione S-transferase) was produced in E. coli and purified by glutathione-sepharose affinity chromatography. Binding of the prodomain of proBDNF (a GST-fusion protein, upper panel) or BDNF (lower panel) was measured to 94 fmol/mm2 immobilized purified Sortilin extracellular domain. The experiment was carried out essentially as described for FIGS. 2-4. The on and off rates—100 to 600 seconds and 600 to 10000 seconds, respectively—were recorded and the Kd values for ligand binding were calculated to ~58 nM for the GST-pro-domain of proBDNF, and ~40 nM for mature BDNF.

Other preparations of mature BDNF have shown Kd values for ligand binding at 10 nM.

DESCRIPTION OF SEQUENCES

SEQ ID NO 1: Sortilin sequence
SEQ ID NO 2: SorLA sequence
SEQ ID NO 3: SorCS1 sequence
SEQ ID NO 4: SorCS3 sequence
SEQ ID NO 5: SorCS2 sequence
SEQ ID NO 6: NGF sequence
SEQ ID NO 7: BDNF sequence
SEQ ID NO 8: neurotrophin-3 sequence
SEQ ID NO 9: neurotrophin-4 sequence
SEQ ID NO 10: neurotensin sequence
SEQ ID NO 11: neuromedin sequence
SEQ ID NO 12: Receptor associated peptide (RAP)
SEQ ID NO 13: pro-neurotensin/pro-neuromedin

DETAILED DESCRIPTION OF THE INVENTION

Definitions

The term "binding" as used herein refers to the transient or longer lasting attraction or binding of two or more moieties to one another, mediated by physical forces such as e.g. electrostatic interactions, hydrophobic interactions, dipole-dipole interactions and hydrogen bonds. The term "hydrophobic interaction" as used herein refers to any interaction occurring between essentially non-polar (hydrophobic) components located within attraction range of one another in a polar environment (e.g. water). As used herein, attraction range is on the scale of about 100 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution. The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding). The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent (input examples relevant to this invention). The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Functional equivalents and variants of polynucleotides encoding a neurotrophin activity modulator and polypeptides comprising such a neurotrophin activity modulator: "functional equivalents" and "variants" are used interchangeably herein. In one preferred embodiment of the invention there is also provided variants of neurotrophin activity modulator and variants of fragments thereof. When being polypeptides, variants are determined on the basis of their degree of identity or their homology with a predetermined amino acid sequence, said predetermined amino acid sequence being one of SEQ ID NO: neurotrophin activity modulator, or, when the variant is a fragment, a fragment of any of the aforementioned amino acid sequences, respectively.

Accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

Sequence identity is determined in one embodiment by utilising fragments of neurotrophin activity modulator peptides comprising at least 25 contiguous amino acids and having an amino acid sequence which is at least 80%, such as 85%, for example 90%, such as 95%, for example 99% identical to the amino acid sequence of any of SEQ ID NO: 2, SEQ ID NO: 4, SEQ ID NO: 6, and SEQ ID NO: 8, respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of SEQ ID NO:1, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO:1 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the neurotrophin activity modulator polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)

ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

"Functional equivalency" as used in the present invention is, according to one preferred embodiment, established by means of reference to the corresponding functionality of a predetermined fragment of the sequence.

Functional equivalents or variants of a neurotrophin activity modulator will be understood to exhibit amino acid sequences gradually differing from the preferred predetermined neurotrophin activity modulator sequence, as the number and scope of insertions, deletions and substitutions including conservative substitutions increase. This difference is measured as a reduction in homology between the preferred predetermined sequence and the fragment or functional equivalent.

All fragments or functional equivalents of SEQ ID NO: neurotrophin activity modulator are included within the scope of this invention, regardless of the degree of homology that they show to the respective, predetermined neurotrophin activity modulator sequences disclosed herein. The reason for this is that some regions of the neurotrophin activity modulator are most likely readily mutatable, or capable of being completely deleted, without any significant effect on the binding activity of the resulting fragment.

A functional variant obtained by substitution may well exhibit some form or degree of native neurotrophin activity modulator activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1-13, respectively, are to be considered as falling within the scope of the present invention when they are preferably at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

Additional factors that may be taken into consideration when determining functional equivalence according to the meaning used herein are i) the ability of antisera to detect a neurotrophin activity modulator fragment according to the present invention, or ii) the ability of the functionally equivalent neurotrophin activity modulator fragment to compete with the corresponding neurotrophin activity modulator in an assay. One method of determining a sequence of immunogenically active amino acids within a known amino acid sequence has been described by Geysen in U.S. Pat. No. 5,595,915 and is incorporated herein by reference.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined neurotrophin activity modulator, or a fragment thereof, it may also be desirable to introduce non-conservative substitutions in any one or more positions of such a neurotrophin activity modulator.

A non-conservative substitution leading to the formation of a functionally equivalent fragment of neurotrophin activity modulator would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa);

and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other neurotrophin activity modulator fragments and/or neurotrophin activity modulator molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of neurotrophin activity modulator according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-neurotrophin activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of neurotrophin activity modulator can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the fragment of neurotrophin activity modulator is synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturers instructions. Solid phase synthesis will enable the incorporation of desirable amino acid substitutions into any fragment of neurotrophin activity modulator according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of neurotrophin activity modulator according to the invention are also provided and fall under the scope of the invention. Neurotrophin activity modulator functional equivalents and variants can be produced as homodimers or heterodimers with other amino acid sequences or with native neurotrophin activity modulator sequences.

Heterodimers include dimers containing immunoreactive neurotrophin activity modulator fragments as well as neurotrophin activity modulator fragments that need not have or exert any biological activity.

Neurotrophin activity modulator fragments according to the invention may be synthesised both in vitro and in vivo. Method for in vitro synthesis are well known, and methods being suitable or suitably adaptable to the synthesis in vivo of neurotrophin activity modulator are also described in the prior art. When synthesized in vivo, a host cell is transformed with vectors containing DNA encoding neurotrophin activity modulator or a fragment thereof. A vector is defined as a replicable nucleic acid construct. Vectors are used to mediate expression of neurotrophin activity modulator. An expression vector is a replicable DNA construct in which a nucleic acid sequence encoding the predetermined neurotrophin activity modulator fragment, or any functional equivalent thereof that can be expressed in vivo, is operably linked to suitable control sequences capable of effecting the expression of the fragment or equivalent in a suitable host. Such control sequences are well known in the art.

Cultures of cells derived from multicellular organisms represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous neurotrophin activity modulator. Cultures of such host cells may be isolated and used as a source of the fragment, or used in therapeutic methods of treatment, including therapeutic methods aimed at promoting or inhibiting a growth state, or diagnostic methods carried out on the human or animal body.

Pharmaceutical agent: the terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent," "pharmaceutical agent" or "drug" or "medicament" is a type of bioactive agent.

The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Treatment: the term "treatment" as used herein refers to a method involving therapy including surgery of a clinical condition in an individual including a human or animal body. The therapy may be prophylactic, ameliorating or curative.

antisense-RNA: an RNA molecule capable of causing gene silencing by specifically binding to an mRNA molecule of interest.

antisense-DNA: a DNA molecule capable of causing gene silencing by specifically binding to an mRNA molecule of interest.

SiRNA: "small interfering RNA" (SiRNA) is a short (often, but not restricted to, less than 30 nucleotides long) double-stranded RNA molecule capable of causing gene-specific silencing in mammalian cells Gene "silencing": a process leading to reduced expression of endogenous genes. Gene silencing is preferably the result of post-transcriptional reduction of gene expression.

Up-regulation of expression: a process leading to increased expression of genes, preferably of endogenous genes.

In vitro/in vivo: the terms are used in their normal meaning.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional bio-molecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

"Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or
ii) a polynucleotide encoding a predetermined amino acid sequence, or
iii) a polynucleotide encoding a fragment of a polypeptide encoded by polynucleotides (i) or (ii), wherein said fragment has at least one predetermined activity as specified herein; and
iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
v) a polynucleotide comprising a nucleotide sequence which is degenerate to the nucleotide sequence of polynucleotides (iii) or (iv);

or the complementary strand of such a polynucleotide.

A "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Detailed Description

The present inventors have identified that neurotrophins bind to receptors of the Vps10p-domain receptor family. Accordingly, the present invention relates to modulation of the activity of at least one neurotrophin.

Without being bound by theory it is believed that Vps10p-domain receptor family is involved in one or more of the following mechanisms in relation to neurotrophins:

Retrograde transport, including uptake of proneurotrophin, neurotrophin and p75

Transport within biosynthetic pathways, including sorting of proneurotrophin and transport from the Golgi network Release of neurotrophins Signalling, including modulation of cellular transport and signalling by formation of ternary complexes with p75 and neurotrophin or pro-neurotrophin Thus, one aspect of the present invention is a method for modulating the activity of at least one neurotrophin and/or a pro-neurotrophin in a single cell or an organism, including an animal, comprising administering to said animal a sufficient amount of an agent capable of binding to a receptor of the Vps10p-domain receptor family or capable of interfering with binding between a receptor of the Vps10p-domain receptor family and a neurotrophin and/or proneurotrophin.

Receptors of the Vps10p-Domain Receptor Family

Figure 1:
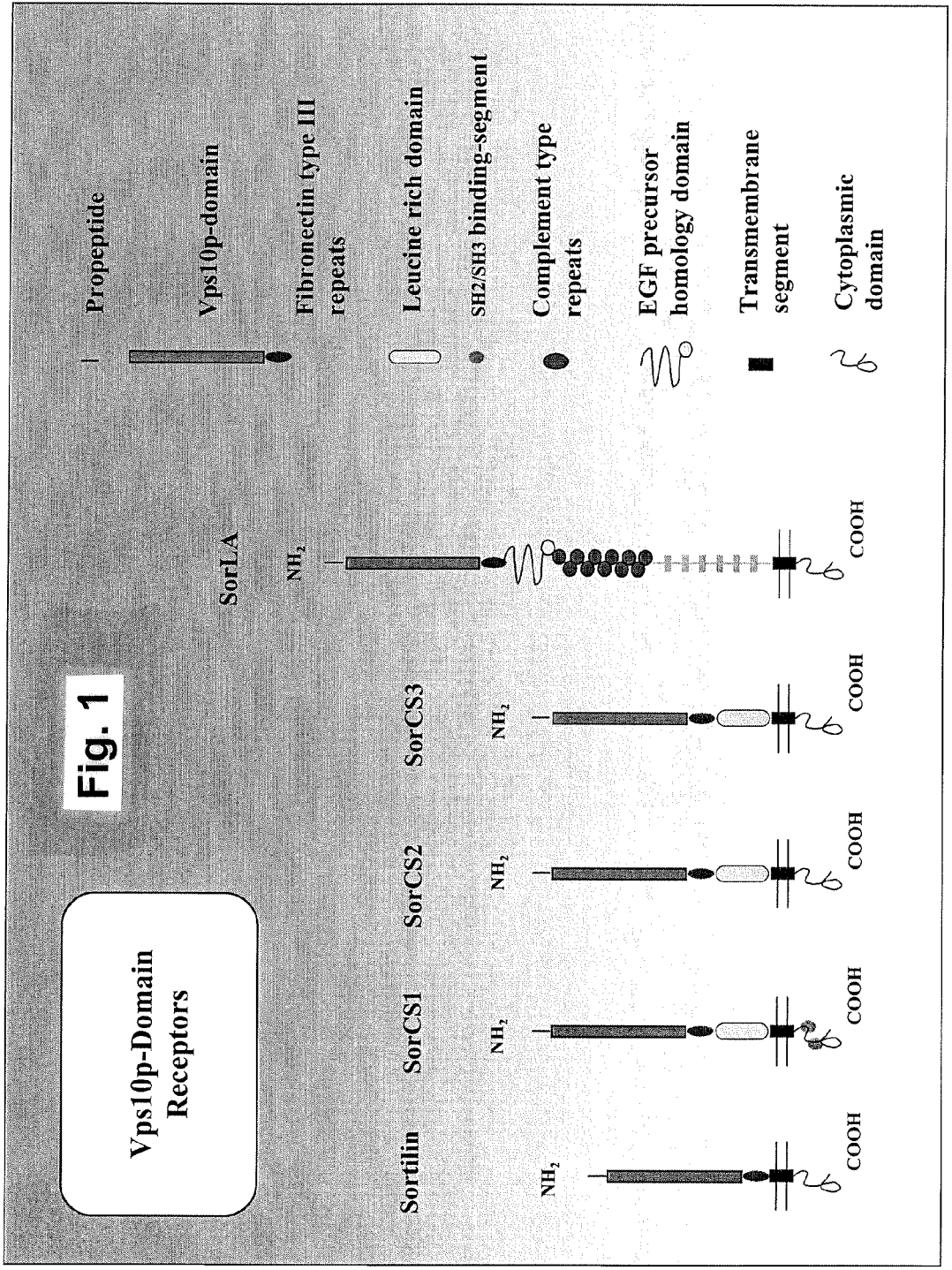
FIG. 1: Examples of Vps10p-domain receptors. Their structural composition is indicated.

The term "receptor of the Vps10p family" refers to a family of receptors characterised by having an N-terminal Vps10p domain; said Vpsp10p domain family comprises SorLA, Sortilin, SorCS1, SorCS-2, or SorCS-3, see FIG. 1. In one embodiment of the present invention, any of the receptors of the Vps10p domain family may be used; more preferably, the receptor comprises the Vps10p domain, the 10CC module, a transmembrane segment as well as a cytoplasmic segment mediating cellular sorting and internalization as well as mediating binding to cytoplasmic adaptors affecting cellular signalling. In particular the receptor used is Sortilin.

Neurotrophins/Pro-Neurotrophins

The term "neurotrophin" as used herein refers to any member of the neurotrophin family, said neurotrophin family comprising neural growth factor (NGF), brain-derived neurotrophic factor (BDNF), neurotrophin-3 (NT-3) and neurotrophin-4/5 (NT-4/5). In one embodiment of the present invention, any member of the neurotrophin family may be used; however, it is preferred that the neurotrophin is NGF or BDNF.

The term "pro-neurotrophin" as used herein may refer to any pro-peptide of the neurotrophin family, said family of pro-peptides comprising pro-NGF, pro-BDNF, pro-NT-3 and pro-NT-4/5. In one embodiment of the present invention, any pro-neurotrophin may be used, however it is preferred that the pro-neurotrophin is pro-NGF or pro-BDNF.

Modulation of Neurotrophin Activity

The terms "neurotrophin-mediated" activity, "activity of a neurotrophin" or "neurotrophin activity" refer to a biological activity that is normally promoted, either directly or indirectly, in the presence of a neurotrophin or a proneurotrophin. Neurotrophin activities include, but are not restricted to, neuronal survival, neuronal differentiation including process formation and neurite outgrowth, biochemical changes such as enzyme induction, involvement in depression and antidepressant action, involvement in accelerating nerve process growth, and involvement in decreasing general cell motility. It has been hypothesized that the lack of neurotrophic factors is responsible for the degeneration of selective neuronal populations as it occurs in Parkinson's disease, Alzheimer's disease and amyotrophic lateral sclerosis.

The activities of pro-neurotrophins include, but are not restricted to, differentially activating both pro- and anti-apoptotic cellular responses, through preferential activation of $p75^{NTR}$ or TrkA receptors respectively.

In preferred embodiments of the present invention, one ore more of these activities of neurotrophin(s) and/or pro-neurotrophin(s) are modulated directly or indirectly by the administration of an agent to an animal.

The terms "modulation" or "modulated" refer to any change or changes in the biological activity of a bioactive agent, for example a neurotrophin. In one embodiment of the present invention, such a modulation of activity of a neurotrophin is a decrease in the neurotrophin activity; however, the modulation may equally be an increase in neurotrophin activity.

Agents Capable of Modulating Activity

In one preferred embodiment of the present invention, an agent is administered to the animal, said agent being capable of modulating the binding between a receptor of the Vps10p-domain receptor family and a neurotrophin and/or pro-neurotrophin.

In another, equally preferred embodiment, the agent is capable of binding to a receptor of the Vps10p-domain receptor family or a neurotrophin and/or pro-neurotrophin thereby interfering with the activity of a neurotrophin, either directly or indirectly.

In a third, equally preferred embodiment of the present invention, the agent is capable of modulating the expression of a receptor of the Vps10p-domain receptor family.

The agent capable of exhibiting one or more of the above mentioned effects may be any type of agent, for example the agent may be selected from the group comprising proteins, peptides, polypeptides, antibodies, antisense-RNA, antisense-DNA, siRNA, other polynucleotides, or organic molecules, In a preferred embodiment the agent is an antibody or a polypeptide, and the agent is most preferably a polypeptide.

In a particularly preferred embodiment of the present invention, the agent administered to the animal is capable of modulating the activity of a sortilin receptor in relation to a neurotrophin, said activity may be, but is not restricted to, one or more of the following:

i) cellular sorting of the receptor ii) receptor binding directly or indirectly by ligand bridging to other receptors, such as the p75 and Trk receptors iii) sortilin receptor signalling In one embodiment of the present invention, the agent is capable of inhibiting binding of a neurotrophin or pro-neurotrophin to a receptor of the Vps10p-domain receptor family. Such inhibition may for example be due to binding of the agent either to the neurotrophin and/or the pro-neurotrophin and/or the receptor.

In one embodiment the agent is capable of binding the neurotrophin and/or proneurotrophin, such as a soluble receptor of the Vps10p-domain receptor family or a fragment or a variant thereof, said fragment or variant being capable of binding said neurotrophin. In particular the soluble receptor is a soluble Sortilin receptor, or a fragment or a variant thereof. Any fragment or variant capable of binding to a neurotrophin and/or a pro-neurotrophin is included herein. In particular a fragment is a peptide comprising a sequence corresponding to the 10CC motif of the Vps10p-domain receptor family having the sequence of SEQ ID NO: 1 amino acid residue 612-740 or a fragment or variant thereof.

In another embodiment the agent is capable of binding to the receptor. The agent may bind to any part of the receptor relevant for inhibiting the binding of the neurotrophin. Accordingly, the agent may be capable of inhibiting the binding of said neurotrophin or said pro-neurotrophin to a receptor of the Vps10p-domain receptor family by binding to an extracellular part of the receptor, an intracellular part of the receptor, or a segment of the transmembrane part of the receptor.

An example of an agent according to the invention is an antibody directed against an extra-cellular part of the receptor. In an even more preferred embodiment, the antibody is purified. In the preferred embodiment wherein the agent is an antibody directed against an extra-cellular part of the receptor, the antibody is preferably directed against a peptide comprising a sequence corresponding to the 10CC motif of the Vps10p-domain receptor family having the sequence of SEQ ID NO: 1 amino acid residue 612-740 or a fragment or variant thereof. In particular the antibody should be directed against a position in this motif so that the antibody sterically blocks the binding of the neurotrophin and/or pro-neurotrophin to the receptor.

In yet another embodiment, the agent is a peptide comprising a sequence having SEQ ID NO: 1 amino acid residue 34-77 corresponding of the part of the pro-Sortilin sequence binding Sortilin or a fragment or variant thereof, said peptide being capable of binding to the receptor. The fragment thereof preferably comprises SEQ ID NO: 1 amino acid residue 50-70, more preferably SEQ ID NO: 1 amino acid residue 55-61 (GVSWGLR).

In another preferred embodiment, the agent is selected from one or more of the following sequences: SEQ ID NO: 2 amino acid residue 29-81 corresponding to the propart from SorLa, or a fragment or a variant thereof. In particular a fragment or a variant thereof should comprise a sequence corresponding to the sequence SEQ ID NO: 2 amino acid residues 47-66.

In yet another preferred embodiment of the present invention, the agent is a peptide which comprises one or more of the following sequences or a fragment or variant thereof: SEQ ID NO: 6 amino acid residue 19-121 (propart for NGF), SEQ ID NO: 7 amino acid residue 19-127 (propart for BDNF), SEQ ID NO: 8 amino acid residue 17-124 (propart for neurotrophin-3 (NT-3), SEQ ID NO: 9 amino acid residue 25-80 (propart for neurotrophin-4 (NT-4), or a fragment or a variant thereof, said peptide being capable of binding to the receptor. The agent is even more preferably a peptide comprising a Sortilin receptor-binding sequence of proNGF or a fragment or variant thereof. The agent in another preferred embodiment may be a peptide comprising the sequence SEQ ID NO: 6 amino acid residue 19-121 (the sequence from the pro-part of NGF) or a fragment or variant thereof, said peptide being capable of binding to the receptor.

In another preferred embodiment of the present invention, the agent may preferably be a peptide having the sequence of SEQ ID NO: 13, the sequence for the pro-neurotensin/pro-neuromedin, SEQ ID NO: 10 (the sequence of neurotensin), SEQ ID NO: 11 (the sequence of neuromedin) or a fragment or a variant thereof, said peptide being capable of binding the receptor.

In yet another preferred embodiment of the present invention the agent may be a peptide comprising an NGF variant or a Sortilin-receptor binding fragment thereof. More preferably, this peptide comprising an NGF variant or a Sortilin-receptor binding fragment thereof is capable of binding Sortilin and stimulating the activity of the Sortilin receptor. Even more preferably, this peptide comprising an NGF variant or a Sortilin-receptor binding fragment thereof comprises one or more of the sequences disclosed in U.S. Pat. No. 6,333,310 or a fragment or variant thereof (sequences for NGF variants).

In yet another embodiment the agent is derived from naturally occurring RAP (receptor-associated protein), such as a fragment or a variant of RAP. RAP (receptor-associated protein) is a cellular protein comprising about 300 amino acids, in a preferred embodiment having the sequence shown in: XM_003315, Gene: AH006949 corresponding to SEQ ID NO: 12. In a preferred embodiment the RAP derived agent is a peptide comprising a minimal functional domain having at most 104 amino acids, preferably from 20 to 60 amino acids. In particular, they are minimal functional protein domains. These peptides have at the most 104 amino acids, preferably from 20 to 60 amino acids. A preferred domain is amino acid positions 219-323 of RAP.

In another preferred embodiment of the present invention, the agent is capable of binding to an intracellular part of the receptor and/or the transmembrane part of a receptor of the Vsp10p domain receptor family. In particular the agent may be capable of binding to the cytoplasmic part of the receptor of the Vsp10p domain receptor family, such as to a part of Sortilin corresponding to SEQ ID NO: 1 amino acid residues 779-831 or a fragment of a variant thereof. More preferably the agent is capable of binding to cytoplasmic part of the receptor of the Vsp10p domain receptor family, such as to a part of Sortilin corresponding to SEQ ID NO: 1 amino acid residues 792-794 (YSVL) or amino acid residues 821-831 (HDDSDEDLLE) or a fragment of a variant thereof.

In particular binding of an agent to the intracellular and transmembrane parts of the receptor may lead to modulation of the neurotrophin and/or proneurotrophin activity through a modulation of the transport of at least one neurotrophin and/or pro-neurotrophin out of, into or within cells expressing the receptor of the Vsp10p domain receptor family as discussed below.

In another preferred embodiment, the agent is capable of modulating the expression of a receptor of the Vps10p-domain receptor family and thereby interfering with the activity of at least one neurotrophin. The modulation may be either inhibition or stimulation of the expression. Preferable methods for modulating the expression of the receptor include, but are not restricted to:

Blocking or inhibiting the activity of the translation products of one or more Vps10p-domain receptor genes and/or one or more derivatives thereof, by inhibiting mRNA translation or transcriptional activation using antisense nucleic acids.

(ii) Inactivating mRNA by ribozymes targeted to the mRNAs encoding one or more Vps10p-domain receptor genes and/or one or more derivatives thereof.

(iii) Inhibition of the intracellularly present translation products of the Vps10p-domain receptor genes by administering molecules which mimic targets of the translation products of one or more Vps10p-domain receptor genes and/or one or more derivatives thereof thereby competing with their natural targets.

(iv) Stimulating the expression of one or more Vps10p-domain receptor genes and/or one or more derivatives thereof, for example in one preferred embodiment, an agent is administered to cells in vitro or in vivo. Such an agent may act either specifically or non-specifically. It is also possible to activate genes responsible for further growth of differentiated tissue by introducing one or more Vps10p-domain receptor genes and/or one or more derivatives thereof into the respective cells and tissue by means of gene therapy. For this purpose the respective nucleic acid sequences may be put under control of a strong promoter, which optionally can be activated and deactivated upon administration of a stimulus to the cell/tissue.

(v) Stimulating expression of one or more Vps10p-domain receptor genes and/or one or more derivatives thereof by administering directly to the respective cell/tissue a translation product, either a peptide or a protein, that is derived from one or more Vps10p-domain receptor gene and/or one or more derivative thereof. Due to the low molecular weight of any of the aforementioned translation products these peptides/proteins can easily be applied to the cell, for example using encapsulation delivery systems.

The change in expression level of the receptor of the Vps10p-domain receptor family may be assayed for using methods known to those skilled in the art, including but not restricted to: DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in (To, Comb. Chem. High Throughput Screen, 2000, 3, 235-41).

Methods for Treating a Disease or Disorder

In one preferred embodiment of the present invention, the invention comprises a method for treating a disease or disorder in an individual. Said method comprises administering to said individual, in a pharmaceutically acceptable carrier, a sufficient amount of an agent capable of interfering with binding between a receptor of the Vps10p-domain receptor family and a neurotrophin and/or proneurotrophin. By "sufficient amount" herein is meant a dose that produces the therapeutic effects for which it is administered. The exact dose will depend on the disorder to be treated, and will be ascertainable by one skilled in the art using known techniques. In general, the agent of the present invention is administered to an animal in an amount of from 1 µg/kg to about 100 mg/kg per day. In addition, as is known in the art, adjustments for age as well as the body weight, general health, sex, diet, time of administration, drug interaction and the severity of the disease may be necessary, and will be ascertainable with routine experimentation by those skilled in the art.

Agents of the present invention are believed to be useful in promoting the development, maintenance, or regeneration of neurons in vitro and in vivo, including central (brain and spinal chord), peripheral (sympathetic, parasympathetic, sensory, and enteric neurons), and motor neurons. Accordingly, agents of the present invention may be utilized in methods for the treatment of a variety of neurological diseases and disorders. In a preferred embodiment, the formulations of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's disease, stroke, ALS, peripheral neuropathies, and other conditions characterized by necrosis or loss of neurons, whether central, peripheral, or motor neurons, in addition to treating damaged nerves due to trauma, burns, kidney dysfunction or injury, pancreatic dysfunction or injury, lung dysfunction or injury, injury to fatty tissue, and the toxic effects of chemotherapeutics used to treat cancer and AIDS. For example, peripheral neuropathies associated with certain conditions, such as neuropathies associated with diabetes, AIDS, or chemotherapy may be treated using the formulations of the present invention.

In various embodiments of the invention, agents are administered to patients in whom the nervous system has been damaged by trauma, surgery, stroke, ischemia, infection, metabolic disease, nutritional deficiency, malignancy, or toxic agents, to promote the survival or growth of neurons, or in whatever conditions are treatable with NGF, NT-3, BDNF or NT4-5. For example, agents of the invention can be used to promote the survival or growth of motor neurons that are damaged by trauma or surgery. Also, agents of the invention can be used to treat motoneuron disorders, such as amyotrophic lateral sclerosis (Lou Gehrig's disease), Bell's palsy, and various conditions involving spinal muscular atrophy, or paralysis. Agents of the present invention can be used to treat human neurodegenerative disorders, such as Alzheimer's disease, Parkinson's disease, epilepsy, multiple sclerosis, Huntington's chorea, Down's Syndrome, nerve deafness, and Meniere's disease. Agents of the present invention can be used as cognitive enhancer, to enhance learning particularly in dementias or trauma. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al. in Brain Cholinergic Systems, M. Steriade and D. Biesold, eds., Oxford University Press, Oxford, pp. 364-386 (1990)). And there are a number of other neurotransmitter systems affected by Alzheimer's disease (Davies Med. Res. Rev. 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al. Neurobiol. Aging 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., Cerebrovasc. and Brain Metab. Rev 1:2 (1989)). Such dementias can be treated by administration of agents of the present invention.

Further, agents of the present invention are preferably used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include, but are not limited to, diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome or AIDS-associated neuropathy; examples of hereditary neuropathies include Charcot-Marie-Tooth disease, Refsum's disease, Abetalipoproteinemia, Tangier disease, Krabbe's disease, Metachromatic leukodystrophy, Down's Syndrome, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine. Other neural diseases that could benefit from treatment with one or more agents of the present invention include depression and mania.

Accordingly, a method of treating a neural disorder in a mammal comprising administering to the mammal a therapeutically effective amount of one or more agents of the present invention is provided.

Methods of Administration

Agents used in the methods of the present invention are generally administered to an animal in the form of a suitable pharmaceutical composition. Accordingly, the present invention also relates to a pharmaceutical composition comprising an agent as defined herein. Such compositions typically contain the agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the agent, use thereof in the compositions is contemplated. Supplementary active compounds can also be incorporated into the compositions.

A pharmaceutical composition of the invention is formulated to be compatible with its intended route of administration. Examples of suitable routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL.™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatine capsules or compressed into tablets. For the purpose of oral therapeutic administration, the agent can be incorporated with excipients and used in the form of tablets, troches, or capsules, oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavouring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agent can also be prepared in the form of suppositories (e.g., with conventional suppository bases such as cocoa butter and other glycerides) or retention enemas for rectal delivery.

In one embodiment, the agent is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit large therapeutic indices are preferred. While agents that exhibit toxic side effects may be used, care should be taken to design a delivery system that targets such agents to the site of affected tissue in order to minimize potential damage to other cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography. With respect to inhibition of Sortilin 10-20 μmol of Neurotensin is used to inhibit Sortilin in a cell culture.

The pharmaceutical compositions can be included in a container, pack, or dispenser together with instructions for administration.

The agents of the present invention can further be inserted into vectors and used in gene therapy. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Vectors suitable for use in gene therapy are known in the art. For example, adenovirus-derived vectors can be used. The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favoured by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7, pp. 109-127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of the agents of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). Adeno-associated viruses exhibit a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as few as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into T cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Other viral vector systems that may be useful for delivery of the agents of the invention are derived from herpes virus, vaccinia virus, and several RNA viruses.

It should be understood that such treatments may also comprise administration of more than one agent, in which case the agents may be either administered concurrently and/or separately.

Animals

In one embodiment of the present invention, agents capable of modulating the activity of a neurotrophin and/or pro-neurotrophin are administered to an animal. Said animal is preferably any animal that expresses a protein of the neurotrophin family, more preferably a mammal, more preferably a domestic animal and most preferably a human being.

Methods for Screening for a Compound which Alters the Binding of at Least One Neurotrophin and/or a Pro-Neurotrophin to a Receptor of the Vps10p-Domain Receptor Family In one preferred embodiment of the present invention, the invention comprises an in vitro method for screening for a compound which alters the binding of at least one neurotrophin and/or a pro-neurotrophin to a receptor of the Vps10p-domain receptor family, said method preferably comprising the steps of:
 a) providing an assay for measuring the binding of a neurotrophin and/or a pro-neurotrophin to a receptor of the Vps10p-domain receptor family
 b) adding the compound to be tested to the assay, and
 c) determining the amount of a neurotrophin and/or a pro-neurotrophin bound to the receptor of the Vps10p-domain receptor family, and
 d) comparing the amount determined in step c) with an amount measured in the absence of the compound to be tested,
 e) wherein a difference in the two amounts identifies a compound which alters the binding of neurotrophins and/or pro-neurotrophins to the receptor of the Vps10p-domain receptor family.

In one preferred embodiment of this screening method of the present invention, the neurotrophin is selected from NGF, BDNF, NT-3 or NT-4/5. Even more preferably, the neurotrophin is NGF or BDNF. The pro-neurotrophin may be selected from proNGF, pro-BDNF, pro-NT-3 or pro-NT-4/5. More preferably, the pro-neurotrophin is pro-NGF or pro-BDNF. In one preferred embodiment of this screening method, the receptor is selected from SorLa, Sortilin, SorCS1, SorCS3, or SorCS2. Even more preferably, the receptor is Sortilin. In another embodiment of the screening method of the present invention, the neurotrophin and/or pro-neurotrophin is capable of binding to an extracellular part of the receptor. The receptor may in one embodiment of the present invention be a receptor that is expressed in a cell, within the plasma membrane and/or presented on a plasma membrane. The cell used in the screening method of the present invention may preferably be selected from primary cultures of neuronal cells, neurone-derived cell-lines, transfected cells capable of expressing receptor of the Vps10p-domain receptor family, peripheral neurons and central neurons. Preferably the cells are immortalised cell lines.

Assays that can be used for measuring the binding of a neurotrophin and/or a pro-neurotrophin to a receptor of the Vps10p-domain receptor family are well-known to those skilled in the art and include, but are not restricted to, yeast two-hybrid assays, competitive binding methods, such as RIAs, ELISAs, and the like. Other tests are Fluorescence resonance energy transfer (FRET), Surface plasmon resonance (Biacore), Western blotting, immunohistochemistry. Results from binding studies can be analyzed using any conventional graphical representation of the binding data, such as Scatchard analysis (Scatchard, Ann. NY Acad. Sci., 51:660-672 [1949]; Goodwin et al., Cell, 73:447-456 [1993]), and the like.

A Method for Determining the Effect of an Agent on Activity of Neurotrophins and/or Pro-Neurotrophins in Cells Presenting a Receptor of the Vps10p-Domain Receptor Family In another embodiment of the present invention, a method is provided for determining the effect of an agent on activity of neurotrophins and/or pro-neurotrophins in cells presenting a receptor of the Vps10p-domain receptor family. Said method comprises the steps of:
 b) administering said agent to a mammal expressing the receptor,
 c) measuring the activity of neurotrophins and/or pro-neurotrophins in said mammal,
 d) comparing the measurement of step b) with a measurement obtained in the absence of the compound to be tested,
 e) wherein the difference in the two measurements identifies the effect of said agent on the activity of neurotrophins on cells presenting receptors of the Vps10p-domain receptor family.

The mammal may express the receptor naturally or may be transfected with the wild-type receptor gene.

The activity of said neurotrophin and/or pro-neurotrophins in said mammal may be measured by one or more of the following measurements:
 a) measuring expression level of a neurotrophin responsive target gene, such as mRNA or protein in tissues of the mammal,
 b) measuring expression level of a receptor as defined herein, such as mRNA or protein in tissues of the mammal
 c) measuring receptor-mediated binding or transport of neurotrophins and/or pro-neurotrophins bound to the receptor,
 d) measuring uptake of neurotrophins and/or pro-neurotrophins into cells of said mammal,
 e) measuring signal transduction from said receptor or a related receptor in cells of said mammal, The related receptor may be p75 receptor or TrkA receptor.

In a preferred embodiment of said method, the method further comprises administering said agent to a mammal lacking expression of said receptor. Said mammal lacking expression of said receptor may only lack expression of said receptor in one or more selected tissues, and/or may have a lowered expression level of said receptor.

Methods for measuring expression of receptor mRNA or protein in tissues of the mammal are well known to those skilled in the art and have been described earlier. Methods for measuring receptor-mediated binding or transport of neurotrophins and/or pro-neurotrophins bound to the receptor are also well-known to those skilled in the art: said methods include, but are not restricted to, yeast two-hybrid screening, Biacore RTM screening, UV cross-linking, and immunoprecipitation.

Methods for measuring the uptake of neurotrophins and/or pro-neurotrophins into cells of a mammal are also well known to those skilled in the art: said methods include but are not restricted to a method wherein neurotrophin/proneurotrophin uptake is measured in cells presenting the receptor and cells not representing the receptor. The neurotrophin/proneurotrophin is preferably labelled, such as labelled radioactively or fluorescently.

A method for Modulating the Transport of at Least One Neurotrophin and/or Pro-Neurotrophin in or into a Neuron of an Animal In another embodiment of the present invention, a method is provided for modulating the transport of at least one neurotrophin and/or pro-neurotrophin out of, or into a cell line or neuron of an animal, said method comprising administering to said animal a sufficient amount of an agent capable of binding a receptor of the Vps10p-domain receptor family. Said modulation may comprise an increase in the anterograde transport of the neurotrophin and/or pro-neurotrophin in the neuron. The modulation may alternatively comprise a decrease in anterograde transport of the neurotrophin and/or pro-neurotrophin in the neuron. In another preferred embodiment, the modulation comprises an increase in the retrograde transport of the neurotrophin and/or pro-neurotrophin in the neuron. In another preferred embodiment, the modulation comprises an decrease in retrograde transport of the neurotrophin and/or pro-neurotrophin in the neuron. The modulation may be conducted by an agent as discussed above.

Soluble Receptor

In yet another aspect the invention relates to a soluble receptor of the Vps10p-domain receptor family or a fragment or a variant thereof, said fragment or variant being capable of binding said neurotrophin. In particular the soluble receptor is a soluble Sortilin receptor, or a fragment or a variant thereof. Furthermore, the invention relates to the use of the soluble receptor. For example the soluble receptor may be used for modulating the activity of neurotrophins and/or pro-neurotrophins, used for modulating the activity of other receptors such as p75 and TrkA. In another embodiment the soluble receptor may be used for diagnostic purposes in relation to neurotrophins and pro-neurotrophins, in particular in relation to NGF and proNGF.

In addition thereto the invention relates to the expression of a receptor as defined herein as well as to the isolation and purification thereof, said methods being conducted by standard methods.

Furthermore, the invention relates to a pharmaceutical composition comprising a soluble receptor of the Vps10p-domain receptor family or a fragment or a variant thereof.

EXAMPLES

Binding to Receptors

All the data provided in FIG. 2-7 are obtained by surface plasmon resonance measurements (BIAcore analysis)

```
                              Sequence listing

SEQ ID NO 1: Sortilin sequence
>sp|Q99523|SORT_HUMAN Sortilin precursor (Glycoprotein 95) (Gp95)
(Neurotensin receptor 3) (NT3) (100 kDa NT receptor)-Homo sapiens
(Human).
MERPWGAADGLSRWPHGLGLLLLLQLLPPSTLSQDRLDAPPPPAAPLPRWSGPIGVSWGL    60

RAAAAGGAFPRGGRWRRSAPGEDEECGRVRDFVAKLANNTHQHVFDDLRGSVSLSWVGDS  120

TGVILVLTTFHVPLVIMTFGQSKLYRSEDYGKNFKDITDLINNTFIRTEFGMAIGPENSG  180
KVVLTAEVSGGSRGGRIFRSSDFAKNFVQTDLPFHPLTQMMYSPQNSDYLLALSTENGLW  240
VSKNFGGKWEEIHKAVCLAKWGSDNTIFFTTYANGSCKADLGALELWRTSDLGKSFKTIG  300
VKIYSFGLGGRFLFASVMADKDTTRRIHVSTDQGDTWSMAQLPSVGQEQFYSILAANDDM  360
VFMHVDEPGDTGFGTIFTSDDRGIVYSKSLDRHLYTTTGGETDFTNVTSLRGVYITSVLS  420
EDNSIQTMITFDQGGRWTHLRKPENSECDATAKNKNECSLHIHASYSISQKLNVPMAPLS  480
EPNAVGIVIAHGSVGDAISVMVPDVYISDDGGYSWTKMLEGPHYYTILDSGGIIVAIEHS  540
SRPINVIKFSTDEGQCWQTYTFTRDPIYFTGLASEPGARSMNISIWGFTESFLTSQWVSY  600
TIDFKDILERNCEEKDYTIWLAHSTDPEDYEDGCILGYKEQFLRLRKSSMCQNGRDYVVT  660
KQPSICLCSLEDFLCDFGYYRPENDSKCVEQPELKGHDLEFCLYGREEHLTTNGYRKIPG  720
DKCQGGVNPVREVKDLKKKCTSNFLSPEKQNSKSNSVPIILAIVGLMLVTVVAGVLIVKK  780
YVCGGRFLVHRYSVLQQHAEANGVDGVDALDTASHTNKSGYHDDSDEDLLE

SEQ ID NO 2: SorLA sequence
>sp|Q92673|SORL_HUMAN Sortilin-related receptor precursor (Sorting
protein-related receptor containing LDLR class A repeats) (SorLA)
(SorLA-1) (Low-density lipoprotein receptor relative with 11 ligand-
binding repeats) (LDLR relative with 11 ligand-binding)
MATRSSRRESRLPFLFTLVALLPPGALCEVWTQRLHGGSAPLPQDRGFLVVQGDPRELRL

WARGDARGASRADEKPLRRKRSAALQPEPIKVYGQVSLNDSHNQMVVHWAGEKSNVIVAL

ARDSLALARPKSSDVYVSYDYGKSFKKISDKLNFGLGNRSEAVIAQFYHSPADNKRYIFA
DAYAQYLWITFDFCNTLQGFSIPFRAADLLLHSKASNLLLGFDRSHPNKQLWKSDDFGQT
WIMIQEHVKSFSWGIDPYDKPNTIYIERHEPSGYSTVFRSTDFFQSRENQEVILEEVRDF
QLRDKYMFATKVVHLLGSEQQSSVQLWVSFGRKPMRAAQFVTRHPINEYYIADASEDQVF
VCVSHSNNRTNLYISEAEGLKFSLSLENVLYYSPGGAGSDTLVRYFANEPFADFHRVEGL
QGVYIATLINGSMNEENMRSVITFDKGGTWEFLQAPAFTGYGEKINCELSQGCSLHLAQR
LSQLLNLQLRRMPILSKESAPGLIIATGSVGKNLASKTNVYISSSAGARWREALPGPHYY
TWGDHGGIITAIAQGMETNELKYSTNEGETWKTFIFSEKPVFVYGLLTEPGEKSTVFTIF
GSNKENVHSWLILQVNATDALGVPCTENDYKLWSPSDERGNECLLGHKTVFKRRTPHATC
FNGEDFDRPVVVSNCSCTREDYECDFGFKMSEDLSLEVCVPDPEFSGKSYSPPVPCPVGS
TYRRTRGYRKISGDTCSGGDVEARLEGELVPCPLAEENEFILYAVRKSIYRYDLASGATE
QLPLTGLRAAVALDFDYEHNCLYWSDLALDVIQRLCLNGSTGQEVIINSGLETVEALAFE
PLSQLLYWVDAGFKKIEVANPDGDFRLTIVNSSVLDRPRALVLVPQEGVMFWTDWGDLKP
GIYRSNMDGSAAYHLVSEDVKWPNGISVDDQWIYWTDAYLECIERITFSGQQRSVILDNL
```

```
PHPYAIAVFKNEIYWDDWSQLSIFRASKYSGSQMEILANQLTGLMDMKIFYKGKNTGSNA
CVPRPCSLLCLPKANNSRSCRCPEDVSSSVLPSGDLMCDCPQGYQLKNNTCVKEENTCLR
NQYRCSNGNCINSIWWCDFDNDCGDMSDERNCPTTICDLDTQFRCQESGTCIPLSYKCDL
EDDCGDNSDESHCEMHQCRSDEYNCSSGMCIRSSWVCDGDNDCRDWSDEANCTAIYHTCE
ASNFQCRNGHCIPQRWACDGDTDCQDGSDEDPVNCEKKCNGFRCPNGTCIPSSKHCDGLR
DCSDGSDEQHCEPLCTHFMDFVCKNRQQCLFHSMVCDGIIQCRDGSDEDAAFAGCSQDPE
FHKVCDEFGFQCQNGVCISLIWKCDGMDDCGDYSDEANCENPTEAPNCSRYFQFRCENGH
CIPNRWKCDRENDCGDWSDEKDCGDSHILPFSTPGPSTCLPNYYRCSSGTCVMDTWVCDG
YRDCADGSDEEACPLLANVTAASTPTQLGRCDRFEFECHQPKTCIPNWKRCDGHQDCQDG
RDEANCPTHSTLTCMSREFQCEDGEACIVLSERCDGFLDCSDESDEKACSDELTVYKVQN
LQWTADFSGDVTLTWMRPKKMPSASCVYNVYYRVVGESIWKTLETHSNKTNTVLKVLKPD
TTYQVKVQVQCLSKAHNTNDFVTLRTPEGLPDAPRNLQLSLPREAEGVIVGHWAPPIHTH
GLIREYIVEYSRSGSKMWASQRAASNFTEIKNLLVNTLYTVRVAAVTSRGIGNWSDSKSI
TTIKGKVIPPPDIHIDSYGENYLSFTLTMESDIKVNGYVVNLFWAFDTHKQERRTLNFRG
SILSHKVGNLTAHTSYEISAWAKTDLGDSPLAFEHVMTRGVRPPAPSLKAKAINQTAVEC
TWTGPRNVVYGIFYATSFLDLYRNPKSLTTSLHNKTVIVSKDEQYLFLVRVVVPYQGPSS
DYVVVKMIPDSRLPPRHLHVVHTGKTSVVIKWESPYDSPDQDLLYAIAVKDLIRKTDRSY
KVKSRNSTVEYTLNKLEPGGKYHIIVQLGNMSKDSSIKITTVSLSAPDALKIITENDHVL
LFWKSLALKEKHFNESRGYEIHMFDSAMNITAYLGNTTDNFFKISNLKMGHNYTFTVQAR
CLFGNQICGEPAILLYDELGSGADASATQAARSTDVAAVVVPILFLILLSLGVGFAILYT
KHRRLQSSFTAFANSHYSSRLGSAIFSSGDDLGEDDEDAPMITGFSDDVPMVIA

SEQ ID NO 3: SorCS1 sequence
>tr|Q8WY21 VPS10 domain receptor SorCS-Homo sapiens (Human).
MGKVGAGGGSQARLSALLAGAGLLILCAPGVCGGGSCCPSPHPSSAPRSAST-
PRGFSHQG RPGRAPATPLPLVVRPLFSVAPGDRALSLERARGTGASMAVAARS-
GRRRRSGADQEKAER GEGASRSPRGVLRDGGQQEPGTRERDPDKATRFR- MEELRLTSTTFALTGDSAHNQAMVHW SGHNSSVILILTKLY-
DYNLGSITESSLWRSTDYGTTYEKLNDKVGLKTILGYLYVCPTNK RKIMLLTDPEI-
ESSLLISSDEGATYQKYRLNFYIQSLLFHPKQEDWILAYSQDQKLYSSA
EFGRRWQLIQEGVVPNRFYWSVMGSNKEPDLVHLEARTVDGHSHYLTCRM-
QNCTEANRNQ PFPGYIDPDSLIVQDHYVFVQLTSGGRPHYYVSYRRNAFAQMK-
LPKYALPKDMHVISTDE NQVFAAVQEWNQNDTYNLYISDTRGVYFTLALEN-
VQSSRGPEGNIMIDLYEVAGIKGMFL ANK-
KIDYQVKTFITYNKGRDWRLLQAPDTDLRGDPVHCLLPYCSLHLHLKVSENPYTSGI
IASKDTAPSIIVASGNIGSELSDTDISMFVSSDAGNTWRQIFEEEHSVLYLDQGGVL-
VAM KHTSLPIRHLWLSFDEGRSWSKYSFTSIPLFVDGVLGEPGEETLIMTVFGHF-
SHRSEWQL VKVDYKSIFDRRCAEEDYRPWQLHSQGEACIMGAKRIYKKRK-
SERKCMQGKYAGAMESEP CVCTEADFDCDYGYERHSNGQCLPAFWFNPSSL-
SKDCSLGQSYLNSTGYRKVVSNNCTDG VREQYTAKPQKCPGKAPRGLRIV-
TADGKLTAEQGHNVTLMVQLEEGDVQRTLIQVDFGDG
IAVSYVNLSSMEDGIKHVYQNVGIFRVTVQVDNSLGSDSAVLYLHVTCPLEHVHL-
SLPFV TTKNKEVNATAVLWPSQVGTLTYVWWYGNNTEPLITLEGSISFRFTSEG-
MNTITVQVSAG NAILQDTKTIAVYEEFRSLRLSFSPNLDDYNPDIPEWRRDIGR-
VIKKSLVEATGVPGQHI LVAVLPGLPTTAELFVLPYQDPAGENKRSTDDLEQISEL-
LIHTLNQNSVHFELKPGVRVL VHAAHL-
TAAPLVDLTPTHSGSAMLMLLSVVFVGLAVFVIYKFKRRVALPSPPSPSTQPGD
SSLRLQRARHATPPSTPKRGSAGAQYAI SEQ ID NO 4: SorCS3 sequence
Ab028982 human sortilin 3
Reference from EMBO 20.no.9 p2180-2190, 2001: description of mRNA for brain
receptor of the Vps10p family,
MEAARTERPAGRPGAPLVRTGLLLLSTWVLAGAEITWDATGGPG RPAA-
PASRPPALSPLSPRAVASQWPEELASARRAAVLGRRAGPELLPQQGGGRG-
GEMQ VEAGGTSPAGERRGRGIPAPAKLGGARRSRRAQPPITQERGDAWA- TAPADGSRGSRPL AKGSREEVKAPRAGGSAAEDLRLPSTSFALTGDSAHNQAM-
VHWSGHNSSVILILTKLY DFNLGSVTESSLWRSTDYGTTYEKLNDKVGLKTVL-
SYLYVNPTNKRKIMLLSDPEMES SILISSDEGATYQKYRLTFYIQSLLFHPKQEDW-
VLAYSLDQKLYSSMDFGRRWQLMHE RITPNRFYWSVAGLDKEADLVH-
MEVRTTDGYAHYLTCRIQECAETTRSGPFARSIDIS SLVVQDEYIFIQVTTSGRA-
SYYVSYRREAFAQIKLPKYSLPKDMHIISTDENQVFAAV QEWNQNDTYNLY-
ISDTRGIYFTLAMENIKSSRGLMGNIIIELYEVAGIKGIFLANKKV DDQVKTY-
ITYNKGRDWRLLQAPDVDLRGSPVHCLLPFCSLHLHLQLSENPYSSGRISS
KETAPGLVVATGNIGPELSYTDIGVFISSDGGNTWRQIFDEEYNVWFLDWGGAL-
VAMK HTPLPVRHLWVSFDEGHSWDKYGFTSVPLFVDGALVEAGMETHIMTVF-
GHFSLRSEWQ LVKVDYKSIFSRHCTKEDYQTWHLLNQGEPCVMGERKIFKKRK-
PGAQCALGRDHSGSV VSEPCVCANWDFECDYGYERHGESQCVPAFWYN-
PASPSKDCSLGQSYLNSTGYRRIVS NNCTDGLREKYTA-
KAQMCPGKAPRGLHVVTTDGRLVAEQGHNATFIILMEEGDLQRTN
IQLDFGDGIAVSYANFSPIEDGIKHVYKSAGIFQVTAYAENNLGSDTAVLFLHVVCPV
EHVHLRVPFVAIRNKEVNISAVVWPSQLGTLTYFWWFGNSTKPLITLDSSISFT-
FLAE GTDTITVQVAAGNALIQDTKEIAVHEYFQSQLLSFSPNLDYHNPDIPEWRK-
DIGNVIK RALVKVTSVPEDQILIAVFPGLPTSAELFILPPKNLTERRKGNEG-
```

-continued

Sequence listing

DLEQIVETLFNAL NQNLVQFELKPGVQVIVYVTQLTLAPLVDSSAGHSSSAMLM-
LLSVVFVGLAVFLIYKF KRKIPWINIYAQVQHDKEQEMIGSVSQSENAPKITLSD-
FTEPEELLDKELDTRVIGGI ATIANSESTKEIPNCTSV

SEQ ID NO 5: SorCS2 sequence
Ab037750 human SorCS2/sortilin 4
Reference from EMBO 20.no.9 p2180-2190, 2001: description of mRNA for brain
receptor of the Vps10p family, related to sortilin and SorLa
LIFHPKEEDKVLAYTKESKLYVSSDLGKKWTLLQERVTKDHVFW
SVSGVDADPDLVHVEAQDLGGDFRYVTCAIHNCSEKMLTAPFAGPIDHGSLT-
VQDDYI FFKATSANQTKYYVSYRRNEFVLMKLPKYALPKDLQIIST-
DESQVFVAVQEWYQMDTY NLYQSDPRGVRY-
ALVLQDVRSSRQAEESVLIDILEVRGVKGVFLANQKIDGKVMTLIT
YNKGRDWDYLRPPSMDMNGKPTNCKPPDCHLHLHLRWADNPYVSGTVHTKD-
TAPGLIM GAGNLGSQLVEYKEEMYITSDCGHTWRQVFEEEHHILYLDHGG-
VIVAIKDTSIPLKIL KFSVDEGLTWSTHNFTSTSVFVDGLLSEPGDETLVMTVF-
GHISFRSDWELVKVDFRPS FSRQCGEEDYSSWELSNLQGDRCIMGQQRSFRK-
RKSTSWCIKGRSFTSALTSRVCECR DSDFLCDYG-
FERSPSSESSTNKCSANFWFNPLSPPDDCALGQTYTSSLGYRKVVSNVC
EGGVDMQQSQVQLQCPLTPPRGLQVSIQGEAVAVRPGEDVLFVVRQEQGDVLT-
TKYQV DLGDGFKAMYVNLTLTGEPIRHRYESPGIYRVSVRAENTAGHDEAV-
LFVQVNSPLQAL YLEVVPVIGLNQEVNLTAVLLPLNPNLTVFYWWIGHSLQPLL-
SLDNSVTTRFSDTGDV RVTVQAACGNSVLQDSRVLRVLDQFQVMPLQFSKEL-
DAYNPNTPEWREDVGLVVTRLL SKETSVPQELLVTVVKPGLPTLAD-
LYVLLPPPRPTRKRSLSSDKRLAAIQQVLNAQKI
SFLLRGGVRVLVALRDTGTGAEQLGGGGGYWAVVVLFVIGLFAAGAFILYKFKRK-
RPG RTVYAQMHNEKEQEMTSPVSHSEDVQGAVQGNHSGVVLSINSREMH-
SYLVS SEQ ID NO 6: NGF sequence
>sp|P01138|NGF_HUMAN Beta-nerve growth factor precursor (Beta-NGF)-
*Homo sapiens* (Human). Signal peptide underlined, propeptide part in
bold italics:
<u>MSMLFYTLITAFLIGIQA</u>*EPHSESNVPAGHTIPQVHWTKLQHSLDTALRRARSAPAAAIA*

*ARVAGQTRNITVDPRLFKKRRLRSPRVLFSTQPPREAADTQDLDFEVGGAAPFNRTHRSK*

*R*SSSHPIFHRGEFSVCDSVSVWVGDKTTATDIKGKEVMVLGEVNINNSVFKQYFFETKCR

DPNPVDSGCRGIDSKHWNSYCTTTHTFVKALTMDGKQAAWRFIRIDTACVCVLSRKAVRR
A

SEQ ID NO 7: BDNF sequence
>gi|114900|sp|P23560|BDNF_HUMAN Brain-derived neurotrophic factor pre-
cursor (BDNF)
<u>MTILFLTMVISYFGCMKA</u>*APMKEANIRGQGGLAYPGVRTHGTLESVNGPKAGSGLTSLAD-*

*TFEHVIEEL*

*LDEDQKVRPNEENNKDADLYTSRVMLSSQVPLEPPLLFLLEEYKNYLDAANMSMRVRR*HS-

DPARRGELSV
CDSISEWVTAADKKTAVDMSGGTVTVLEKVPVSKGQLKQYFYETKCNPMGYTKEGCRGID-
KRHWNSQCRT
TQSYVRALTMDSKKRIGWRFIRIDTSCVCTLTIKRGR

SEQ ID NO 8: neurotrophin-3 sequence
>gi|128581|sp|P20783|NT3_HUMAN Neurotrophin-3 precursor
(NT-3) (Neurotrophic factor) (HDNF) (Nerve growth factor
2) (NGF-2)
<u>MSILFYVIFLAYLRGI</u>*QGNNMDQRSLPEDSLNSLIIKLIQADILKNKLSKQMVD-*

*VKENYQSTLPKAEAPR*

*EPERGGPAKSAFQPVIAMDTELLRQQRRYNSPRVLLSDSTPLEPPPLYLMEDYVG-*

*SPVVANRTSRRKRYA*

EHKSHRGEYSVCDSESLWVTDKSSAIDIRGHQVTVLGEIKTGNSPVKQYFYETR-
CKEARPVKNGCRGIDD
KHWNSQCKTSQTYVRALTSENNKLVGWRWIRIDTSCVCALSRKIGRT

Sequence listing

SEQ ID NO 9: neurotrophin-4 sequence
>gi|462741|sp|P34130|NT5_HUMAN Neurotrophin-5 precursor
(NT-5) (Neutrophic factor 5) (Neurotrophin-4) (NT-4)
(Neutrophic factor 4)
MLPLPSCSLPILLLFLLPSVPIESQPPPSTLPPFLAPEWDLLSPRVVLSRGAPAGP-

PLLFLLEAGAFRES

AGAPANRSRRGVSETAPASRRGELAVCDAVSGWVTDRRTAVDLRGREVEVL-
GEVPAAGGSPLRQYFFETR
CKADNAEEGGPGAGGGGCRGVDRRHWVSECKAKQSYVRALTADAQGRVGWRWIRID-
TACVCTLLSRTGRA

SEQ ID NO 10: neurotensin sequence
qlyenkprrp yil

SEQ ID NO 11: neuromedin sequence
ipyil

SEQ ID NO 12: Receptor associated peptide (RAP)
  1 maprrvrsfl rglpalllll lflgpwpaas hggkysrekn qpkpspkres geefrmekln
 61 qlwekaqrlh lppvrlaelh adlkiqerde lawkklkldg ldedgekear lirnlnvila
121 kygldgkkda rqvtsnslsg tqedglddpr leklwhkakt sgkfsgeeld klwreflhhk
181 ekvheynvll etlsrteeih envispsdls dikgsvlhsr htelkeklrs inqgldrlrr
241 vshqgystea efeeprvidl wdlaqsanlt dkeleafree lkhfeakiek hnhyqkqlei
301 aheklrhaes vgdgervsrs rekhallegr tkelgytvkk hlqdlsgris rarhnel SEQ ID NO 13: pro-neurotensin/pro-neuromedin
>gi|2828196|sp|P30990|NEUT_HUMAN Neurotensin/neuromedin N precursor [Contains: Large neuromedin N (NmN-125); Neuromedin N (NmN) (NN); Neurotensin (NT); Tail peptide]
MMAGMKIQLVCMLLLAFSSWSLCSDSEEEMKALEADFLTNMHTSKISKAHVPSWK
MTLLNVCSLVNNLNS
PAEETGEVHEEELVARRKLPTALDGFSLEAMLTIYQLHKICHSRAFQHWELIQEDIL
DTGNDKNGKEEVI KRKIPYILKRQLYENKPRRPYILKRDSYYY

---

The invention claimed is:

1. A method for inhibiting the binding of a pro-neurotrophin to a sortilin receptor, wherein said method comprises administering an inhibitorily effective amount of an antibody which binds to an extracellular part of said receptor to an animal suffering from neurons that are damaged by trauma or surgery, thereby inhibiting the binding of the pro-neurotriphin to said receptor, wherein the pro-neurotrophin is selected from the group consisting of brain derived pro-neurotrophic factor (Pro-BDNF), pro-neurotrophin-3 (pro-NT-3) and pro-neurotrophin-4/5 (pro-NT-4/5).

2. The method of claim 1, wherein the animal is human.

3. The method of claim 1, wherein the antibody binds to a peptide comprising amino acid residues 612-740 of SEQ ID NO:1.

4. The method of claim 1, wherein the antibody binds to a peptide comprising amino acid residues 24-77 of SEQ ID NO:1.

5. The method of claim 1, wherein the antibody is administered in an amount of from 1 µg/kg to about 100 mg/kg per day.

6. The method of claim 1, wherein the pro-neurotrophin is brain derived pro-neurotrophic factor (Pro-BDNF).

7. The method of claim 1, wherein the pro-neurotrophin is pro-neurotrophin-3 (pro-NT-3).

8. The method of claim 1, wherein the pro-neurotrophin is pro-neurotrophin-4/5 (pro-NT-4/5).

* * * * *

SEQUENCE LISTING

<160> NUMBER OF SEQ ID NOS: 13

<210> SEQ ID NO 1
<211> LENGTH: 831
<212> TYPE: PRT
<213> ORGANISM: Homo sapiens

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
            35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu

-continued

```
            130                 135                 140
Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                    165                 170                 175

Glu Asn Ser Gly Lys Val Val Leu Thr Ala Glu Val Ser Gly Gly Ser
                180                 185                 190

Arg Gly Gly Arg Ile Phe Arg Ser Ser Asp Phe Ala Lys Asn Phe Val
            195                 200                 205

Gln Thr Asp Leu Pro Phe His Pro Leu Thr Gln Met Met Tyr Ser Pro
210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
                260                 265                 270

Ala Asn Gly Ser Cys Lys Ala Asp Leu Gly Ala Leu Glu Leu Trp Arg
            275                 280                 285

Thr Ser Asp Leu Gly Lys Ser Phe Lys Thr Ile Gly Val Lys Ile Tyr
290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
                340                 345                 350

Ile Leu Ala Ala Asn Asp Asp Met Val Phe Met His Val Asp Glu Pro
            355                 360                 365

Gly Asp Thr Gly Phe Gly Thr Ile Phe Thr Ser Asp Asp Arg Gly Ile
370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
                420                 425                 430

Gln Gly Gly Arg Trp Thr His Leu Arg Lys Pro Glu Asn Ser Glu Cys
            435                 440                 445

Asp Ala Thr Ala Lys Asn Lys Asn Glu Cys Ser Leu His Ile His Ala
450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
                500                 505                 510

Tyr Ser Trp Thr Lys Met Leu Glu Gly Pro His Tyr Tyr Thr Ile Leu
            515                 520                 525

Asp Ser Gly Gly Ile Ile Val Ala Ile Glu His Ser Ser Arg Pro Ile
530                 535                 540

Asn Val Ile Lys Phe Ser Thr Asp Glu Gly Gln Cys Trp Gln Thr Tyr
545                 550                 555                 560
```

```
Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Met Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

<210> SEQ ID NO 2
<211> LENGTH: 2214
<212> TYPE: PRT
<213> ORGANISM: Homo sapiens

<400> SEQUENCE: 2

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
```

```
            100                 105                 110
Lys Ser Asn Val Ile Val Ala Leu Ala Arg Asp Ser Leu Ala Leu Ala
            115                 120                 125

Arg Pro Lys Ser Ser Asp Val Tyr Val Ser Tyr Asp Tyr Gly Lys Ser
            130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                    165                 170                 175

Tyr Ile Phe Ala Asp Ala Tyr Ala Gln Tyr Leu Trp Ile Thr Phe Asp
                180                 185                 190

Phe Cys Asn Thr Leu Gln Gly Phe Ser Ile Pro Phe Arg Ala Ala Asp
            195                 200                 205

Leu Leu Leu His Ser Lys Ala Ser Asn Leu Leu Gly Phe Asp Arg
            210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                    245                 250                 255

Pro Tyr Asp Lys Pro Asn Thr Ile Tyr Ile Glu Arg His Glu Pro Ser
                260                 265                 270

Gly Tyr Ser Thr Val Phe Arg Ser Thr Asp Phe Phe Gln Ser Arg Glu
            275                 280                 285

Asn Gln Glu Val Ile Leu Glu Glu Val Arg Asp Phe Gln Leu Arg Asp
            290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                    325                 330                 335

Ala Ala Gln Phe Val Thr Arg His Pro Ile Asn Glu Tyr Tyr Ile Ala
                340                 345                 350

Asp Ala Ser Glu Asp Gln Val Phe Val Cys Val Ser His Ser Asn Asn
            355                 360                 365

Arg Thr Asn Leu Tyr Ile Ser Glu Ala Glu Gly Leu Lys Phe Ser Leu
370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                    405                 410                 415

Val Glu Gly Leu Gln Gly Val Tyr Ile Ala Thr Leu Ile Asn Gly Ser
                420                 425                 430

Met Asn Glu Glu Asn Met Arg Ser Val Ile Thr Phe Asp Lys Gly Gly
            435                 440                 445

Thr Trp Glu Phe Leu Gln Ala Pro Ala Phe Thr Gly Tyr Gly Glu Lys
            450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                    485                 490                 495

Lys Glu Ser Ala Pro Gly Leu Ile Ile Ala Thr Gly Ser Val Gly Lys
                500                 505                 510

Asn Leu Ala Ser Lys Thr Asn Val Tyr Ile Ser Ser Ser Ala Gly Ala
            515                 520                 525
```

```
Arg Trp Arg Glu Ala Leu Pro Gly Pro His Tyr Tyr Thr Trp Gly Asp
            530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
                595                 600                 605

Ser Trp Leu Ile Leu Gln Val Asn Ala Thr Asp Ala Leu Gly Val Pro
610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
                660                 665                 670

Ser Asn Cys Ser Cys Thr Arg Glu Asp Tyr Glu Cys Asp Phe Gly Phe
                675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
                740                 745                 750

Pro Leu Ala Glu Glu Asn Glu Phe Ile Leu Tyr Ala Val Arg Lys Ser
                755                 760                 765

Ile Tyr Arg Tyr Asp Leu Ala Ser Gly Ala Thr Glu Gln Leu Pro Leu
770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
                820                 825                 830

Thr Val Glu Ala Leu Ala Phe Glu Pro Leu Ser Gln Leu Leu Tyr Trp
                835                 840                 845

Val Asp Ala Gly Phe Lys Lys Ile Glu Val Ala Asn Pro Asp Gly Asp
850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
                900                 905                 910

Tyr His Leu Val Ser Glu Asp Val Lys Trp Pro Asn Gly Ile Ser Val
                915                 920                 925

Asp Asp Gln Trp Ile Tyr Trp Thr Asp Ala Tyr Leu Glu Cys Ile Glu
930                 935                 940
```

-continued

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
            965                 970                 975

Asp Trp Ser Gln Leu Ser Ile Phe Arg Ala Ser Lys Tyr Ser Gly Ser
            980                 985                 990

Gln Met Glu Ile Leu Ala Asn Gln Leu Thr Gly Leu Met Asp Met Lys
        995                 1000                1005

Ile Phe Tyr Lys Gly Lys Asn Thr Gly Ser Asn Ala Cys Val Pro
    1010                1015                1020

Arg Pro Cys Ser Leu Leu Cys Leu Pro Lys Ala Asn Asn Ser Arg
    1025                1030                1035

Ser Cys Arg Cys Pro Glu Asp Val Ser Ser Val Leu Pro Ser
    1040                1045                1050

Gly Asp Leu Met Cys Asp Cys Pro Gln Gly Tyr Gln Leu Lys Asn
    1055                1060                1065

Asn Thr Cys Val Lys Glu Glu Asn Thr Cys Leu Arg Asn Gln Tyr
    1070                1075                1080

Arg Cys Ser Asn Gly Asn Cys Ile Asn Ser Ile Trp Trp Cys Asp
    1085                1090                1095

Phe Asp Asn Asp Cys Gly Asp Met Ser Asp Glu Arg Asn Cys Pro
    1100                1105                1110

Thr Thr Ile Cys Asp Leu Asp Thr Gln Phe Arg Cys Gln Glu Ser
    1115                1120                1125

Gly Thr Cys Ile Pro Leu Ser Tyr Lys Cys Asp Leu Glu Asp Asp
    1130                1135                1140

Cys Gly Asp Asn Ser Asp Glu Ser His Cys Glu Met His Gln Cys
    1145                1150                1155

Arg Ser Asp Glu Tyr Asn Cys Ser Ser Gly Met Cys Ile Arg Ser
    1160                1165                1170

Ser Trp Val Cys Asp Gly Asp Asn Asp Cys Arg Asp Trp Ser Asp
    1175                1180                1185

Glu Ala Asn Cys Thr Ala Ile Tyr His Thr Cys Glu Ala Ser Asn
    1190                1195                1200

Phe Gln Cys Arg Asn Gly His Cys Ile Pro Gln Arg Trp Ala Cys
    1205                1210                1215

Asp Gly Asp Thr Asp Cys Gln Asp Gly Ser Asp Glu Asp Pro Val
    1220                1225                1230

Asn Cys Glu Lys Lys Cys Asn Gly Phe Arg Cys Pro Asn Gly Thr
    1235                1240                1245

Cys Ile Pro Ser Ser Lys His Cys Asp Gly Leu Arg Asp Cys Ser
    1250                1255                1260

Asp Gly Ser Asp Glu Gln His Cys Glu Pro Leu Cys Thr His Phe
    1265                1270                1275

Met Asp Phe Val Cys Lys Asn Arg Gln Gln Cys Leu Phe His Ser
    1280                1285                1290

Met Val Cys Asp Gly Ile Ile Gln Cys Arg Asp Gly Ser Asp Glu
    1295                1300                1305

Asp Ala Ala Phe Ala Gly Cys Ser Gln Asp Pro Glu Phe His Lys
    1310                1315                1320

Val Cys Asp Glu Phe Gly Phe Gln Cys Gln Asn Gly Val Cys Ile
    1325                1330                1335

Ser Leu Ile Trp Lys Cys Asp Gly Met Asp Asp Cys Gly Asp Tyr

-continued

```
              1340                1345                1350
Ser Asp Glu Ala Asn Cys Glu Asn Pro Thr Glu Ala Pro Asn Cys
    1355                1360                1365
Ser Arg Tyr Phe Gln Phe Arg Cys Glu Asn Gly His Cys Ile Pro
    1370                1375                1380
Asn Arg Trp Lys Cys Asp Arg Glu Asn Asp Cys Gly Asp Trp Ser
    1385                1390                1395
Asp Glu Lys Asp Cys Gly Asp Ser His Ile Leu Pro Phe Ser Thr
    1400                1405                1410
Pro Gly Pro Ser Thr Cys Leu Pro Asn Tyr Tyr Arg Cys Ser Ser
    1415                1420                1425
Gly Thr Cys Val Met Asp Thr Trp Val Cys Asp Gly Tyr Arg Asp
    1430                1435                1440
Cys Ala Asp Gly Ser Asp Glu Glu Ala Cys Pro Leu Leu Ala Asn
    1445                1450                1455
Val Thr Ala Ala Ser Thr Pro Thr Gln Leu Gly Arg Cys Asp Arg
    1460                1465                1470
Phe Glu Phe Glu Cys His Gln Pro Lys Thr Cys Ile Pro Asn Trp
    1475                1480                1485
Lys Arg Cys Asp Gly His Gln Asp Cys Gln Asp Gly Arg Asp Glu
    1490                1495                1500
Ala Asn Cys Pro Thr His Ser Thr Leu Thr Cys Met Ser Arg Glu
    1505                1510                1515
Phe Gln Cys Glu Asp Gly Glu Ala Cys Ile Val Leu Ser Glu Arg
    1520                1525                1530
Cys Asp Gly Phe Leu Asp Cys Ser Asp Glu Ser Asp Glu Lys Ala
    1535                1540                1545
Cys Ser Asp Glu Leu Thr Val Tyr Lys Val Gln Asn Leu Gln Trp
    1550                1555                1560
Thr Ala Asp Phe Ser Gly Asp Val Thr Leu Thr Trp Met Arg Pro
    1565                1570                1575
Lys Lys Met Pro Ser Ala Ser Cys Val Tyr Asn Val Tyr Tyr Arg
    1580                1585                1590
Val Val Gly Glu Ser Ile Trp Lys Thr Leu Glu Thr His Ser Asn
    1595                1600                1605
Lys Thr Asn Thr Val Leu Lys Val Leu Lys Pro Asp Thr Thr Tyr
    1610                1615                1620
Gln Val Lys Val Gln Val Gln Cys Leu Ser Lys Ala His Asn Thr
    1625                1630                1635
Asn Asp Phe Val Thr Leu Arg Thr Pro Glu Gly Leu Pro Asp Ala
    1640                1645                1650
Pro Arg Asn Leu Gln Leu Ser Leu Pro Arg Glu Ala Glu Gly Val
    1655                1660                1665
Ile Val Gly His Trp Ala Pro Pro Ile His Thr His Gly Leu Ile
    1670                1675                1680
Arg Glu Tyr Ile Val Glu Tyr Ser Arg Ser Gly Ser Lys Met Trp
    1685                1690                1695
Ala Ser Gln Arg Ala Ala Ser Asn Phe Thr Glu Ile Lys Asn Leu
    1700                1705                1710
Leu Val Asn Thr Leu Tyr Thr Val Arg Val Ala Ala Val Thr Ser
    1715                1720                1725
Arg Gly Ile Gly Asn Trp Ser Asp Ser Lys Ser Ile Thr Thr Ile
    1730                1735                1740
```

```
Lys Gly Lys Val Ile Pro Pro Asp Ile His Ile Asp Ser Tyr
1745             1750            1755

Gly Glu Asn Tyr Leu Ser Phe Thr Leu Thr Met Glu Ser Asp Ile
1760             1765            1770

Lys Val Asn Gly Tyr Val Val Asn Leu Phe Trp Ala Phe Asp Thr
1775             1780            1785

His Lys Gln Glu Arg Arg Thr Leu Asn Phe Arg Gly Ser Ile Leu
1790             1795            1800

Ser His Lys Val Gly Asn Leu Thr Ala His Thr Ser Tyr Glu Ile
1805             1810            1815

Ser Ala Trp Ala Lys Thr Asp Leu Gly Asp Ser Pro Leu Ala Phe
1820             1825            1830

Glu His Val Met Thr Arg Gly Val Arg Pro Pro Ala Pro Ser Leu
1835             1840            1845

Lys Ala Lys Ala Ile Asn Gln Thr Ala Val Glu Cys Thr Trp Thr
1850             1855            1860

Gly Pro Arg Asn Val Val Tyr Gly Ile Phe Tyr Ala Thr Ser Phe
1865             1870            1875

Leu Asp Leu Tyr Arg Asn Pro Lys Ser Leu Thr Thr Ser Leu His
1880             1885            1890

Asn Lys Thr Val Ile Val Ser Lys Asp Glu Gln Tyr Leu Phe Leu
1895             1900            1905

Val Arg Val Val Val Pro Tyr Gln Gly Pro Ser Ser Asp Tyr Val
1910             1915            1920

Val Val Lys Met Ile Pro Asp Ser Arg Leu Pro Pro Arg His Leu
1925             1930            1935

His Val Val His Thr Gly Lys Thr Ser Val Val Ile Lys Trp Glu
1940             1945            1950

Ser Pro Tyr Asp Ser Pro Asp Gln Asp Leu Leu Tyr Ala Ile Ala
1955             1960            1965

Val Lys Asp Leu Ile Arg Lys Thr Asp Arg Ser Tyr Lys Val Lys
1970             1975            1980

Ser Arg Asn Ser Thr Val Glu Tyr Thr Leu Asn Lys Leu Glu Pro
1985             1990            1995

Gly Gly Lys Tyr His Ile Ile Val Gln Leu Gly Asn Met Ser Lys
2000             2005            2010

Asp Ser Ser Ile Lys Ile Thr Thr Val Ser Leu Ser Ala Pro Asp
2015             2020            2025

Ala Leu Lys Ile Ile Thr Glu Asn Asp His Val Leu Leu Phe Trp
2030             2035            2040

Lys Ser Leu Ala Leu Lys Glu Lys His Phe Asn Glu Ser Arg Gly
2045             2050            2055

Tyr Glu Ile His Met Phe Asp Ser Ala Met Asn Ile Thr Ala Tyr
2060             2065            2070

Leu Gly Asn Thr Thr Asp Asn Phe Phe Lys Ile Ser Asn Leu Lys
2075             2080            2085

Met Gly His Asn Tyr Thr Phe Thr Val Gln Ala Arg Cys Leu Phe
2090             2095            2100

Gly Asn Gln Ile Cys Gly Glu Pro Ala Ile Leu Leu Tyr Asp Glu
2105             2110            2115

Leu Gly Ser Gly Ala Asp Ala Ser Ala Thr Gln Ala Ala Arg Ser
2120             2125            2130
```

-continued

Thr Asp Val Ala Ala Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210

<210> SEQ ID NO 3
<211> LENGTH: 1168
<212> TYPE: PRT
<213> ORGANISM: Homo sapiens

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
                35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
                100                 105                 110

Ala Asp Gln Glu Lys Ala Glu Arg Gly Glu Gly Ala Ser Arg Ser Pro
                115                 120                 125

Arg Gly Val Leu Arg Asp Gly Gly Gln Gln Glu Pro Gly Thr Arg Glu
        130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
                195                 200                 205

Arg Ser Thr Asp Tyr Gly Thr Thr Tyr Glu Lys Leu Asn Asp Lys Val
        210                 215                 220

Gly Leu Lys Thr Ile Leu Gly Tyr Leu Tyr Val Cys Pro Thr Asn Lys
225                 230                 235                 240

Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
                260                 265                 270

Tyr Ile Gln Ser Leu Leu Phe His Pro Lys Gln Glu Asp Trp Ile Leu
                275                 280                 285

```
Ala Tyr Ser Gln Asp Gln Lys Leu Tyr Ser Ala Glu Phe Gly Arg
    290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
                340                 345                 350
Cys Thr Glu Ala Asn Arg Asn Gln Pro Phe Pro Gly Tyr Ile Asp Pro
            355                 360                 365
Asp Ser Leu Ile Val Gln Asp His Tyr Val Phe Val Gln Leu Thr Ser
    370                 375                 380
Gly Gly Arg Pro His Tyr Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
                420                 425                 430
Asn Asp Thr Tyr Asn Leu Tyr Ile Ser Asp Thr Arg Gly Val Tyr Phe
            435                 440                 445
Thr Leu Ala Leu Glu Asn Val Gln Ser Ser Arg Gly Pro Glu Gly Asn
    450                 455                 460
Ile Met Ile Asp Leu Tyr Glu Val Ala Gly Ile Lys Gly Met Phe Leu
465                 470                 475                 480
Ala Asn Lys Lys Ile Asp Tyr Gln Val Lys Thr Phe Ile Thr Tyr Asn
                485                 490                 495
Lys Gly Arg Asp Trp Arg Leu Leu Gln Ala Pro Asp Thr Asp Leu Arg
            500                 505                 510
Gly Asp Pro Val His Cys Leu Leu Pro Tyr Cys Ser Leu His Leu His
    515                 520                 525
Leu Lys Val Ser Glu Asn Pro Tyr Thr Ser Gly Ile Ile Ala Ser Lys
    530                 535                 540
Asp Thr Ala Pro Ser Ile Ile Val Ala Ser Gly Asn Ile Gly Ser Glu
545                 550                 555                 560
Leu Ser Asp Thr Asp Ile Ser Met Phe Val Ser Ser Asp Ala Gly Asn
                565                 570                 575
Thr Trp Arg Gln Ile Phe Glu Glu Glu His Ser Val Leu Tyr Leu Asp
            580                 585                 590
Gln Gly Gly Val Leu Val Ala Met Lys His Thr Ser Leu Pro Ile Arg
                595                 600                 605
His Leu Trp Leu Ser Phe Asp Glu Gly Arg Ser Trp Ser Lys Tyr Ser
    610                 615                 620
Phe Thr Ser Ile Pro Leu Phe Val Asp Gly Val Leu Gly Glu Pro Gly
625                 630                 635                 640
Glu Glu Thr Leu Ile Met Thr Val Phe Gly His Phe Ser His Arg Ser
                645                 650                 655
Glu Trp Gln Leu Val Lys Val Asp Tyr Lys Ser Ile Phe Asp Arg Arg
            660                 665                 670
Cys Ala Glu Glu Asp Tyr Arg Pro Trp Gln Leu His Ser Gln Gly Glu
        675                 680                 685
Ala Cys Ile Met Gly Ala Lys Arg Ile Tyr Lys Lys Arg Lys Ser Glu
    690                 695                 700
```

```
Arg Lys Cys Met Gln Gly Lys Tyr Ala Gly Ala Met Glu Ser Glu Pro
705                 710                 715                 720

Cys Val Cys Thr Glu Ala Asp Phe Asp Cys Asp Tyr Gly Tyr Glu Arg
            725                 730                 735

His Ser Asn Gly Gln Cys Leu Pro Ala Phe Trp Phe Asn Pro Ser Ser
        740                 745                 750

Leu Ser Lys Asp Cys Ser Leu Gly Gln Ser Tyr Leu Asn Ser Thr Gly
        755                 760                 765

Tyr Arg Lys Val Val Ser Asn Cys Thr Asp Gly Val Arg Glu Gln
    770                 775                 780

Tyr Thr Ala Lys Pro Gln Lys Cys Pro Gly Lys Ala Pro Arg Gly Leu
785             790                 795                 800

Arg Ile Val Thr Ala Asp Gly Lys Leu Thr Ala Glu Gln Gly His Asn
                805                 810                 815

Val Thr Leu Met Val Gln Leu Glu Glu Gly Asp Val Gln Arg Thr Leu
                820                 825                 830

Ile Gln Val Asp Phe Gly Asp Gly Ile Ala Val Ser Tyr Val Asn Leu
                835                 840                 845

Ser Ser Met Glu Asp Gly Ile Lys His Val Tyr Gln Asn Val Gly Ile
850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
                900                 905                 910

Leu Trp Pro Ser Gln Val Gly Thr Leu Thr Tyr Val Trp Trp Tyr Gly
            915                 920                 925

Asn Asn Thr Glu Pro Leu Ile Thr Leu Glu Gly Ser Ile Ser Phe Arg
930                 935                 940

Phe Thr Ser Glu Gly Met Asn Thr Ile Thr Val Gln Val Ser Ala Gly
945                 950                 955                 960

Asn Ala Ile Leu Gln Asp Thr Lys Thr Ile Ala Val Tyr Glu Glu Phe
            965                 970                 975

Arg Ser Leu Arg Leu Ser Phe Ser Pro Asn Leu Asp Asp Tyr Asn Pro
            980                 985                 990

Asp Ile Pro Glu Trp Arg Arg Asp Ile Gly Arg Val Ile Lys Lys Ser
            995                 1000                1005

Leu Val Glu Ala Thr Gly Val Pro Gly Gln His Ile Leu Val Ala
    1010                1015                1020

Val Leu Pro Gly Leu Pro Thr Thr Ala Glu Leu Phe Val Leu Pro
    1025                1030                1035

Tyr Gln Asp Pro Ala Gly Glu Asn Lys Arg Ser Thr Asp Asp Leu
    1040                1045                1050

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
```

-continued

```
                1115                1120                1125

Pro Ser Pro Pro Ser Pro Ser Thr Gln Pro Gly Asp Ser Ser Leu
            1130                1135                1140

Arg Leu Gln Arg Ala Arg His Ala Thr Pro Pro Ser Thr Pro Lys
        1145                1150                1155

Arg Gly Ser Ala Gly Ala Gln Tyr Ala Ile
        1160                1165

<210> SEQ ID NO 4
<211> LENGTH: 1222
<212> TYPE: PRT
<213> ORGANISM: Homo sapiens

<400> SEQUENCE: 4

Met Glu Ala Ala Arg Thr Glu Arg Pro Ala Gly Arg Pro Gly Ala Pro
1               5                   10                  15

Leu Val Arg Thr Gly Leu Leu Leu Ser Thr Trp Val Leu Ala Gly
                20                  25                  30

Ala Glu Ile Thr Trp Asp Ala Thr Gly Gly Pro Gly Arg Pro Ala Ala
            35                  40                  45

Pro Ala Ser Arg Pro Pro Ala Leu Ser Pro Leu Ser Pro Arg Ala Val
        50                  55                  60

Ala Ser Gln Trp Pro Glu Glu Leu Ala Ser Arg Arg Ala Ala Val
65                  70                  75                  80

Leu Gly Arg Arg Ala Gly Pro Glu Leu Leu Pro Gln Gln Gly Gly
                85                  90                  95

Arg Gly Gly Glu Met Gln Val Glu Ala Gly Thr Ser Pro Ala Gly
                100                 105                 110

Glu Arg Arg Gly Arg Gly Ile Pro Ala Pro Ala Lys Leu Gly Gly Ala
            115                 120                 125

Arg Arg Ser Arg Arg Ala Gln Pro Pro Ile Thr Gln Glu Arg Gly Asp
        130                 135                 140

Ala Trp Ala Thr Ala Pro Ala Asp Gly Ser Arg Gly Ser Arg Pro Leu
145                 150                 155                 160

Ala Lys Gly Ser Arg Glu Glu Val Lys Ala Pro Arg Ala Gly Gly Ser
                165                 170                 175

Ala Ala Glu Asp Leu Arg Leu Pro Ser Thr Ser Phe Ala Leu Thr Gly
            180                 185                 190

Asp Ser Ala His Asn Gln Ala Met Val His Trp Ser Gly His Asn Ser
        195                 200                 205

Ser Val Ile Leu Ile Leu Thr Lys Leu Tyr Asp Phe Asn Leu Gly Ser
        210                 215                 220

Val Thr Glu Ser Ser Leu Trp Arg Ser Thr Asp Tyr Gly Thr Thr Tyr
225                 230                 235                 240

Glu Lys Leu Asn Asp Lys Val Gly Leu Lys Thr Val Leu Ser Tyr Leu
                245                 250                 255

Tyr Val Asn Pro Thr Asn Lys Arg Lys Ile Met Leu Leu Ser Asp Pro
            260                 265                 270

Glu Met Glu Ser Ser Ile Leu Ile Ser Ser Asp Glu Gly Ala Thr Tyr
        275                 280                 285

Gln Lys Tyr Arg Leu Thr Phe Tyr Ile Gln Ser Leu Leu Phe His Pro
        290                 295                 300

Lys Gln Glu Asp Trp Val Leu Ala Tyr Ser Leu Asp Gln Lys Leu Tyr
305                 310                 315                 320
```

```
Ser Ser Met Asp Phe Gly Arg Arg Trp Gln Leu Met His Glu Arg Ile
            325                 330                 335

Thr Pro Asn Arg Phe Tyr Trp Ser Val Ala Gly Leu Asp Lys Glu Ala
            340                 345                 350

Asp Leu Val His Met Glu Val Arg Thr Thr Asp Gly Tyr Ala His Tyr
            355                 360                 365

Leu Thr Cys Arg Ile Gln Glu Cys Ala Glu Thr Thr Arg Ser Gly Pro
370                 375                 380

Phe Ala Arg Ser Ile Asp Ile Ser Ser Leu Val Val Gln Asp Glu Tyr
385                 390                 395                 400

Ile Phe Ile Gln Val Thr Thr Ser Gly Arg Ala Ser Tyr Tyr Val Ser
            405                 410                 415

Tyr Arg Arg Glu Ala Phe Ala Gln Ile Lys Leu Pro Lys Tyr Ser Leu
            420                 425                 430

Pro Lys Asp Met His Ile Ile Ser Thr Asp Glu Asn Gln Val Phe Ala
            435                 440                 445

Ala Val Gln Glu Trp Asn Gln Asn Asp Thr Tyr Asn Leu Tyr Ile Ser
450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Glu Leu Tyr Glu Val Ala
            485                 490                 495

Gly Ile Lys Gly Ile Phe Leu Ala Asn Lys Lys Val Asp Asp Gln Val
            500                 505                 510

Lys Thr Tyr Ile Thr Tyr Asn Lys Gly Arg Asp Trp Arg Leu Leu Gln
            515                 520                 525

Ala Pro Asp Val Asp Leu Arg Gly Ser Pro Val His Cys Leu Leu Pro
530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
            565                 570                 575

Thr Gly Asn Ile Gly Pro Glu Leu Ser Tyr Thr Asp Ile Gly Val Phe
            580                 585                 590

Ile Ser Ser Asp Gly Gly Asn Thr Trp Arg Gln Ile Phe Asp Glu Glu
            595                 600                 605

Tyr Asn Val Trp Phe Leu Asp Trp Gly Gly Ala Leu Val Ala Met Lys
            610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
            645                 650                 655

Gly Ala Leu Val Glu Ala Gly Met Glu Thr His Ile Met Thr Val Phe
            660                 665                 670

Gly His Phe Ser Leu Arg Ser Glu Trp Gln Leu Val Lys Val Asp Tyr
            675                 680                 685

Lys Ser Ile Phe Ser Arg His Cys Thr Lys Glu Asp Tyr Gln Thr Trp
            690                 695                 700

His Leu Leu Asn Gln Gly Glu Pro Cys Val Met Gly Glu Arg Lys Ile
705                 710                 715                 720

Phe Lys Lys Arg Lys Pro Gly Ala Gln Cys Ala Leu Gly Arg Asp His
            725                 730                 735

Ser Gly Ser Val Val Ser Glu Pro Cys Val Cys Ala Asn Trp Asp Phe
```

-continued

```
                740                 745                 750
Glu Cys Asp Tyr Gly Tyr Glu Arg His Gly Glu Ser Gln Cys Val Pro
            755                 760                 765
Ala Phe Trp Tyr Asn Pro Ala Ser Pro Ser Lys Asp Cys Ser Leu Gly
        770                 775                 780
Gln Ser Tyr Leu Asn Ser Thr Gly Tyr Arg Arg Ile Val Ser Asn Asn
785                 790                 795                 800
Cys Thr Asp Gly Leu Arg Glu Lys Tyr Thr Ala Lys Ala Gln Met Cys
                805                 810                 815
Pro Gly Lys Ala Pro Arg Gly Leu His Val Val Thr Thr Asp Gly Arg
            820                 825                 830
Leu Val Ala Glu Gln Gly His Asn Ala Thr Phe Ile Ile Leu Met Glu
        835                 840                 845
Glu Gly Asp Leu Gln Arg Thr Asn Ile Gln Leu Asp Phe Gly Asp Gly
    850                 855                 860
Ile Ala Val Ser Tyr Ala Asn Phe Ser Pro Ile Glu Asp Gly Ile Lys
865                 870                 875                 880
His Val Tyr Lys Ser Ala Gly Ile Phe Gln Val Thr Ala Tyr Ala Glu
                885                 890                 895
Asn Asn Leu Gly Ser Asp Thr Ala Val Leu Phe Leu His Val Val Cys
            900                 905                 910
Pro Val Glu His Val His Leu Arg Val Pro Phe Val Ala Ile Arg Asn
        915                 920                 925
Lys Glu Val Asn Ile Ser Ala Val Val Trp Pro Ser Gln Leu Gly Thr
    930                 935                 940
Leu Thr Tyr Phe Trp Trp Phe Gly Asn Ser Thr Lys Pro Leu Ile Thr
945                 950                 955                 960
Leu Asp Ser Ser Ile Ser Phe Thr Phe Leu Ala Glu Gly Thr Asp Thr
                965                 970                 975
Ile Thr Val Gln Val Ala Ala Gly Asn Ala Leu Ile Gln Asp Thr Lys
            980                 985                 990
Glu Ile Ala Val His Glu Tyr Phe Gln Ser Gln Leu Leu Ser Phe Ser
        995                 1000                1005
Pro Asn Leu Asp Tyr His Asn Pro Asp Ile Pro Glu Trp Arg Lys
    1010                1015                1020
Asp Ile Gly Asn Val Ile Lys Arg Ala Leu Val Lys Val Thr Ser
    1025                1030                1035
Val Pro Glu Asp Gln Ile Leu Ile Ala Val Phe Pro Gly Leu Pro
    1040                1045                1050
Thr Ser Ala Glu Leu Phe Ile Leu Pro Pro Lys Asn Leu Thr Glu
    1055                1060                1065
Arg Arg Lys Gly Asn Glu Gly Asp Leu Glu Gln Ile Val Glu Thr
    1070                1075                1080
Leu Phe Asn Ala Leu Asn Gln Asn Leu Val Gln Phe Glu Leu Lys
    1085                1090                1095
Pro Gly Val Gln Val Ile Val Tyr Val Thr Gln Leu Thr Leu Ala
    1100                1105                1110
Pro Leu Val Asp Ser Ser Ala Gly His Ser Ser Ser Ala Met Leu
    1115                1120                1125
Met Leu Leu Ser Val Val Phe Val Gly Leu Ala Val Phe Leu Ile
    1130                1135                1140
Tyr Lys Phe Lys Arg Lys Ile Pro Trp Ile Asn Ile Tyr Ala Gln
    1145                1150                1155
```

```
Val Gln His Asp Lys Glu Gln Glu Met Ile Gly Ser Val Ser Gln
    1160            1165                1170

Ser Glu Asn Ala Pro Lys Ile Thr Leu Ser Asp Phe Thr Glu Pro
    1175            1180                1185

Glu Glu Leu Leu Asp Lys Glu Leu Asp Thr Arg Val Ile Gly Gly
    1190            1195                1200

Ile Ala Thr Ile Ala Asn Ser Glu Ser Thr Lys Glu Ile Pro Asn
    1205            1210                1215

Cys Thr Ser Val
    1220

<210> SEQ ID NO 5
<211> LENGTH: 907
<212> TYPE: PRT
<213> ORGANISM: Homo sapiens

<400> SEQUENCE: 5

Leu Ile Phe His Pro Lys Glu Asp Lys Val Leu Ala Tyr Thr Lys
1               5                   10                  15

Glu Ser Lys Leu Tyr Val Ser Ser Asp Leu Gly Lys Lys Trp Thr Leu
            20                  25                  30

Leu Gln Glu Arg Val Thr Lys Asp His Val Phe Trp Ser Val Ser Gly
            35                  40                  45

Val Asp Ala Asp Pro Asp Leu Val His Val Glu Ala Gln Asp Leu Gly
        50                  55                  60

Gly Asp Phe Arg Tyr Val Thr Cys Ala Ile His Asn Cys Ser Glu Lys
65                  70                  75                  80

Met Leu Thr Ala Pro Phe Ala Gly Pro Ile Asp His Gly Ser Leu Thr
                85                  90                  95

Val Gln Asp Asp Tyr Ile Phe Phe Lys Ala Thr Ser Ala Asn Gln Thr
            100                 105                 110

Lys Tyr Tyr Val Ser Tyr Arg Arg Asn Glu Phe Val Leu Met Lys Leu
        115                 120                 125

Pro Lys Tyr Ala Leu Pro Lys Asp Leu Gln Ile Ile Ser Thr Asp Glu
    130                 135                 140

Ser Gln Val Phe Val Ala Val Gln Glu Trp Tyr Gln Met Asp Thr Tyr
145                 150                 155                 160

Asn Leu Tyr Gln Ser Asp Pro Arg Gly Val Arg Tyr Ala Leu Val Leu
                165                 170                 175

Gln Asp Val Arg Ser Ser Arg Gln Ala Glu Glu Ser Val Leu Ile Asp
            180                 185                 190

Ile Leu Glu Val Arg Gly Val Lys Gly Val Phe Leu Ala Asn Gln Lys
        195                 200                 205

Ile Asp Gly Lys Val Met Thr Leu Ile Thr Tyr Asn Lys Gly Arg Asp
    210                 215                 220

Trp Asp Tyr Leu Arg Pro Pro Ser Met Asp Met Asn Gly Lys Pro Thr
225                 230                 235                 240

Asn Cys Lys Pro Pro Asp Cys His Leu His Leu His Leu Arg Trp Ala
                245                 250                 255

Asp Asn Pro Tyr Val Ser Gly Thr Val His Thr Lys Asp Thr Ala Pro
            260                 265                 270

Gly Leu Ile Met Gly Ala Gly Asn Leu Gly Ser Gln Leu Val Glu Tyr
        275                 280                 285

Lys Glu Glu Met Tyr Ile Thr Ser Asp Cys Gly His Thr Trp Arg Gln
```

-continued

```
                 290                 295                 300
Val Phe Glu Glu His His Ile Leu Tyr Leu Asp His Gly Gly Val
305                 310                 315                 320

Ile Val Ala Ile Lys Asp Thr Ser Ile Pro Leu Lys Ile Leu Lys Phe
                325                 330                 335

Ser Val Asp Glu Gly Leu Thr Trp Ser Thr His Asn Phe Thr Ser Thr
                340                 345                 350

Ser Val Phe Val Asp Gly Leu Leu Ser Glu Pro Gly Asp Glu Thr Leu
                355                 360                 365

Val Met Thr Val Phe Gly His Ile Ser Phe Arg Ser Asp Trp Glu Leu
                370                 375                 380

Val Lys Val Asp Phe Arg Pro Ser Phe Ser Arg Gln Cys Gly Glu Glu
385                 390                 395                 400

Asp Tyr Ser Ser Trp Glu Leu Ser Asn Leu Gln Gly Asp Arg Cys Ile
                405                 410                 415

Met Gly Gln Gln Arg Ser Phe Arg Lys Arg Lys Ser Thr Ser Trp Cys
                420                 425                 430

Ile Lys Gly Arg Ser Phe Thr Ser Ala Leu Thr Ser Arg Val Cys Glu
                435                 440                 445

Cys Arg Asp Ser Asp Phe Leu Cys Asp Tyr Gly Phe Glu Arg Ser Pro
450                 455                 460

Ser Ser Glu Ser Ser Thr Asn Lys Cys Ser Ala Asn Phe Trp Phe Asn
465                 470                 475                 480

Pro Leu Ser Pro Pro Asp Asp Cys Ala Leu Gly Gln Thr Tyr Thr Ser
                485                 490                 495

Ser Leu Gly Tyr Arg Lys Val Val Ser Asn Val Cys Glu Gly Gly Val
                500                 505                 510

Asp Met Gln Gln Ser Gln Val Gln Leu Gln Cys Pro Leu Thr Pro Pro
                515                 520                 525

Arg Gly Leu Gln Val Ser Ile Gln Gly Glu Ala Val Ala Val Arg Pro
                530                 535                 540

Gly Glu Asp Val Leu Phe Val Val Arg Gln Glu Gln Gly Asp Val Leu
545                 550                 555                 560

Thr Thr Lys Tyr Gln Val Asp Leu Gly Asp Gly Phe Lys Ala Met Tyr
                565                 570                 575

Val Asn Leu Thr Leu Thr Gly Glu Pro Ile Arg His Arg Tyr Glu Ser
                580                 585                 590

Pro Gly Ile Tyr Arg Val Ser Val Arg Ala Glu Asn Thr Ala Gly His
                595                 600                 605

Asp Glu Ala Val Leu Phe Val Gln Val Asn Ser Pro Leu Gln Ala Leu
                610                 615                 620

Tyr Leu Glu Val Val Pro Val Ile Gly Leu Asn Gln Glu Val Asn Leu
625                 630                 635                 640

Thr Ala Val Leu Leu Pro Leu Asn Pro Asn Leu Thr Val Phe Tyr Trp
                645                 650                 655

Trp Ile Gly His Ser Leu Gln Pro Leu Leu Ser Leu Asp Asn Ser Val
                660                 665                 670

Thr Thr Arg Phe Ser Asp Thr Gly Asp Val Arg Val Thr Val Gln Ala
                675                 680                 685

Ala Cys Gly Asn Ser Val Leu Gln Asp Ser Arg Val Leu Arg Val Leu
                690                 695                 700

Asp Gln Phe Gln Val Met Pro Leu Gln Phe Ser Lys Glu Leu Asp Ala
705                 710                 715                 720
```

```
Tyr Asn Pro Asn Thr Pro Glu Trp Arg Glu Asp Val Gly Leu Val Val
                725                 730                 735

Thr Arg Leu Leu Ser Lys Glu Thr Ser Val Pro Gln Glu Leu Leu Val
            740                 745                 750

Thr Val Val Lys Pro Gly Leu Pro Thr Leu Ala Asp Leu Tyr Val Leu
        755                 760                 765

Leu Pro Pro Arg Pro Thr Arg Lys Arg Ser Leu Ser Ser Asp Lys
770                 775                 780

Arg Leu Ala Ala Ile Gln Gln Val Leu Asn Ala Gln Lys Ile Ser Phe
785                 790                 795                 800

Leu Leu Arg Gly Gly Val Arg Val Leu Val Ala Leu Arg Asp Thr Gly
                805                 810                 815

Thr Gly Ala Glu Gln Leu Gly Gly Gly Gly Tyr Trp Ala Val Val
            820                 825                 830

Val Leu Phe Val Ile Gly Leu Phe Ala Ala Gly Ala Phe Ile Leu Tyr
        835                 840                 845

Lys Phe Lys Arg Lys Arg Pro Gly Arg Thr Val Tyr Ala Gln Met His
    850                 855                 860

Asn Glu Lys Glu Gln Glu Met Thr Ser Pro Val Ser His Ser Glu Asp
865                 870                 875                 880

Val Gln Gly Ala Val Gln Gly Asn His Ser Gly Val Val Leu Ser Ile
                885                 890                 895

Asn Ser Arg Glu Met His Ser Tyr Leu Val Ser
                900                 905

<210> SEQ ID NO 6
<211> LENGTH: 241
<212> TYPE: PRT
<213> ORGANISM: Homo sapiens

<400> SEQUENCE: 6

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Val His Trp Thr Lys Leu Gln His Ser Leu Asp Thr Ala Leu
            35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
                100                 105                 110

Phe Asn Arg Thr His Arg Ser Lys Arg Ser Ser Ser His Pro Ile Phe
            115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
```

180                 185                 190
Asp Ser Lys His Trp Asn Ser Tyr Cys Thr Thr Thr His Thr Phe Val
        195                 200                 205

Lys Ala Leu Thr Met Asp Gly Lys Gln Ala Trp Arg Phe Ile Arg
        210                 215                 220

Ile Asp Thr Ala Cys Val Cys Val Leu Ser Arg Lys Ala Val Arg Arg
225                 230                 235                 240

Ala

<210> SEQ ID NO 7
<211> LENGTH: 246
<212> TYPE: PRT
<213> ORGANISM: Homo sapiens

<400> SEQUENCE: 7

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Gly Leu Thr Ser Leu Ala Asp Thr Phe Glu His
    50                  55                  60

Val Ile Glu Glu Leu Leu Asp Glu Asp Gln Lys Val Arg Pro Asn Glu
65                  70                  75                  80

Glu Asn Asn Lys Asp Ala Asp Leu Tyr Thr Ser Arg Val Met Leu Ser
                85                  90                  95

Ser Gln Val Pro Leu Glu Pro Pro Leu Leu Phe Leu Leu Glu Glu Tyr
            100                 105                 110

Lys Asn Tyr Leu Asp Ala Ala Asn Met Ser Met Arg Val Arg Arg His
        115                 120                 125

Ser Asp Pro Ala Arg Arg Gly Glu Leu Ser Val Cys Asp Ser Ile Ser
    130                 135                 140

Glu Trp Val Thr Ala Ala Asp Lys Lys Thr Ala Val Asp Met Ser Gly
145                 150                 155                 160

Gly Thr Val Thr Val Leu Glu Lys Val Pro Val Ser Lys Gly Gln Leu
                165                 170                 175

Lys Gln Tyr Phe Tyr Glu Thr Lys Cys Asn Pro Met Gly Tyr Thr Lys
            180                 185                 190

Glu Gly Cys Arg Gly Ile Asp Lys Arg His Trp Asn Ser Gln Cys Arg
        195                 200                 205

Thr Thr Gln Ser Tyr Val Arg Ala Leu Thr Met Asp Ser Lys Lys Arg
    210                 215                 220

Ile Gly Trp Arg Phe Ile Arg Ile Asp Thr Ser Cys Val Cys Thr Leu
225                 230                 235                 240

Thr Ile Lys Arg Gly Arg
                245

<210> SEQ ID NO 8
<211> LENGTH: 257
<212> TYPE: PRT
<213> ORGANISM: Homo sapiens

<400> SEQUENCE: 8

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 9
<211> LENGTH: 210
<212> TYPE: PRT
<213> ORGANISM: Homo sapiens

<400> SEQUENCE: 9

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Pro Ser Thr Leu Pro
            20                  25                  30

Pro Phe Leu Ala Pro Glu Trp Asp Leu Leu Ser Pro Arg Val Val Leu
        35                  40                  45

Ser Arg Gly Ala Pro Ala Gly Pro Pro Leu Leu Phe Leu Leu Glu Ala
50                  55                  60

Gly Ala Phe Arg Glu Ser Ala Gly Ala Pro Ala Asn Arg Ser Arg Arg
65                  70                  75                  80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110

Leu Arg Gly Arg Glu Val Glu Val Leu Gly Glu Val Pro Ala Ala Gly
        115                 120                 125

```
Gly Ser Pro Leu Arg Gln Tyr Phe Glu Thr Arg Cys Lys Ala Asp
        130                 135                 140

Asn Ala Glu Glu Gly Gly Pro Gly Ala Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
                180                 185                 190

Ile Arg Ile Asp Thr Ala Cys Val Cys Thr Leu Leu Ser Arg Thr Gly
                195                 200                 205

Arg Ala
    210

<210> SEQ ID NO 10
<211> LENGTH: 13
<212> TYPE: PRT
<213> ORGANISM: Homo sapiens

<400> SEQUENCE: 10

Gln Leu Tyr Glu Asn Lys Pro Arg Arg Pro Tyr Ile Leu
1               5                   10

<210> SEQ ID NO 11
<211> LENGTH: 5
<212> TYPE: PRT
<213> ORGANISM: Homo sapiens

<400> SEQUENCE: 11

Ile Pro Tyr Ile Leu
1               5

<210> SEQ ID NO 12
<211> LENGTH: 357
<212> TYPE: PRT
<213> ORGANISM: Homo sapiens

<400> SEQUENCE: 12

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
                20                  25                  30

Gly Lys Tyr Ser Arg Glu Lys Asn Gln Pro Lys Pro Ser Pro Lys Arg
            35                  40                  45

Glu Ser Gly Glu Glu Phe Arg Met Glu Lys Leu Asn Gln Leu Trp Glu
50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
                100                 105                 110

Arg Asn Leu Asn Val Ile Leu Ala Lys Tyr Gly Leu Asp Gly Lys Lys
            115                 120                 125

Asp Ala Arg Gln Val Thr Ser Asn Ser Leu Ser Gly Thr Gln Glu Asp
        130                 135                 140

Gly Leu Asp Asp Pro Arg Leu Glu Lys Leu Trp His Lys Ala Lys Thr
145                 150                 155                 160
```

```
Ser Gly Lys Phe Ser Gly Glu Glu Leu Asp Lys Leu Trp Arg Glu Phe
            165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
            195                 200                 205

Leu Ser Asp Ile Lys Gly Ser Val Leu His Ser Arg His Thr Glu Leu
            210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
            245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
            275                 280                 285

Glu Lys His Asn His Tyr Gln Lys Gln Leu Glu Ile Ala His Glu Lys
            290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
            325                 330                 335

Thr Val Lys Lys His Leu Gln Asp Leu Ser Gly Arg Ile Ser Arg Ala
            340                 345                 350

Arg His Asn Glu Leu
            355

<210> SEQ ID NO 13
<211> LENGTH: 170
<212> TYPE: PRT
<213> ORGANISM: Homo sapiens

<400> SEQUENCE: 13

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
            20                  25                  30

Leu Glu Ala Asp Phe Leu Thr Asn Met His Thr Ser Lys Ile Ser Lys
            35                  40                  45

Ala His Val Pro Ser Trp Lys Met Thr Leu Leu Asn Val Cys Ser Leu
            50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
            85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
            115                 120                 125

Thr Gly Asn Asp Lys Asn Gly Lys Glu Glu Val Ile Lys Arg Lys Ile
            130                 135                 140
```

-continued

```
Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165             170
```